US012655197B2

(12) United States Patent
Liu et al.

(10) Patent No.: US 12,655,197 B2
(45) Date of Patent: Jun. 16, 2026

(54) INTEGRIN-TARGETING PROTEIN AND METHODS OF USE THEREOF

(71) Applicants: GEORGIA STATE UNIVERSITY RESEARCH FOUNDATION, INC., Atlanta, GA (US); PRODA BIOTECH LLC, Marietta, GA (US)

(72) Inventors: Zhi-Ren Liu, Marietta, GA (US); Chakra Ravi Turaga, Atlanta, GA (US); Jenny Yang, Marietta, GA (US)

(73) Assignees: GEORGIA STATE UNIVERSITY RESEARCH FOUNDATION, INC., Atlanta, GA (US); PRODA BIOTECH LLC, Marietta, GA (US)

( * ) Notice: Subject to any disclaimer, the term of this patent is extended or adjusted under 35 U.S.C. 154(b) by 0 days.

(21) Appl. No.: 15/555,442

(22) PCT Filed: Mar. 4, 2016

(86) PCT No.: PCT/US2016/021037
§ 371 (c)(1),
(2) Date: Sep. 1, 2017

(87) PCT Pub. No.: WO2016/144815
PCT Pub. Date: Sep. 15, 2016

(65) Prior Publication Data
US 2018/0044403 A1      Feb. 15, 2018

Related U.S. Application Data

(60) Provisional application No. 62/129,499, filed on Mar. 6, 2015.

(51) Int. Cl.
C07K 14/705 (2006.01)
A61K 38/00 (2006.01)
A61K 38/17 (2006.01)
A61K 47/60 (2017.01)

(52) U.S. Cl.
CPC .... C07K 14/70557 (2013.01); A61K 38/1774 (2013.01); A61K 47/60 (2017.08); C07K 14/70546 (2013.01); A61K 38/00 (2013.01)

(58) Field of Classification Search
None
See application file for complete search history.

(56) References Cited

U.S. PATENT DOCUMENTS

2004/0265305 A1* 12/2004 Vaishnaw ............... A61K 45/06
424/144.1
2013/0281357 A1* 10/2013 Liu ......................... A61P 43/00
530/410

FOREIGN PATENT DOCUMENTS

EP        1988915 A1 * 11/2008    ............. A61P 11/00

OTHER PUBLICATIONS

Yin, Lu, Dissertation "Rational Design and Development of Anti-Angiogenic Protein Agents." Dissertation, Georgia State University, 2011. https://scholarworks.gsu.edu/biology_diss/109. pp. 1-280. (Year: 2011).*
Turaga et al. Rational design of a protein that binds integrin αvβ3 outside the ligand binding site. Nat Commun . May 31, 2016;7:11675. (Year: 2016).*
Sun et al. Functional glycan-free adhesion domain of human cell surface receptor CD58: design, production and NMR studies. The EMBO Journal vol. 18 No. 11 pp. 2941-2949, 1999. (Year: 1999).*
Maeshima and Makino. Angiogenesis and chronic kidney disease. Fibrogenesis & Tissue Repair 2010, 3:13, pp. 1-17. (Year: 2010).*
UniProtKB/Swiss-Prot: P06729.2. locus CD2_Human, accession P06729; Jun. 17, 2020, pp. 1-8 (Year: 2020).*
Maeshima et al. Extracellular Matrix-derived Peptide Binds to αvβ3 Integrin and Inhibits Angiogenesis. J Biol Chem. Aug. 24, 2001;276(34):31959-68. (Year: 2001).*
He et al. Exploration of peptide T7 and its derivative as integrin αvβ3-targeted imaging agents. OncoTargets and Therapy 2015:8 1483-1491. (Year: 2015).*
Burgess et al. Reduction of Tumstatin in Asthmatic Airways Contributes to Angiogenesis, Inflammation, and Hyperresponsiveness. Am J Respir Crit Care Med vol. 181. pp 106-115, 2010 (Year: 2010).*
Eikesdal et al. Identification of amino acids essential for the antiangiogenic activity of tumstatin and its use in combination antitumor activity. PNAS Sep. 30, 2008 105 (39) 15040-15045. (Year: 2008).*
Kuntz. Structure-based strategies for drug design and discovery. Science. 1992 257(5073):1078-1082. (Year: 1992).*
NP_036962. Kanatsu-Shinohara et al. T-cell surface antigen CD2 precursor [Rattus norvegicus]. pp. 3. Jul. 5, 2021. (Year: 2021).*
Turaga, Ravi C., "Proagio (A Protein Designed to Target Integrin αvβ3)." Thesis, Georgia State University, 2017. (Year: 2017).*
Sharma et al. Simultaneously targeting cancer-associated fibroblasts and angiogenic vessel as a treatment for TNBC. J. Exp. Med. 218(4):e20200712, Feb. 9, 2021. (Year: 2021).*
Kuziel et al., "Alterations in the mammary gland and tumor microenvironment of formerly obese mice", BMC Cancer. Dec. 1, 2023;23(1):1183. doi: 10.1186/s12885-023-11688-3.
Zhao et al., "α-smooth muscle actin is not a marker of fibrogenic cell activity in skeletal muscle fibrosis", PLoS One. Jan. 10, 2018;13(1):e0191031. doi: 10.1371/journal.pone.0191031. eCollection 2018.
Office Action received in corresponding CA Application No. 2,978,597, mailed Nov. 7, 2025, 4 pages.

* cited by examiner

Primary Examiner — Maher M Haddad
(74) Attorney, Agent, or Firm — Judy Jarecki-Black; Sharon Ngwenya

(57)        ABSTRACT

A non-toxic anti-angiogenesis protein that inhibits tumor growth and exhibits in vitro activity in induction of angiogenic endothelial cell apoptosis without targeting VEGF/VEGFR or any other RTK pathways is described. The protein targets integrins $\alpha_v\beta_3$, at a groove in the βA domain of $\beta_3$ formed by α2 helix, B—C loop, and α2-α3 loop.

12 Claims, 49 Drawing Sheets
Specification includes a Sequence Listing.

Intermolecular energies of D1-CD2 variants

| D1-CD2 | Mutations | $(\Delta E)^{a}$(Kcal/mol) |
|---|---|---|
| Wild | Wild | – |
| Variant 1 | L94N, E95D, K96V, I97C, F98N, D99F, L100A, K101S, I102R | −131.35 |
| Variant 2 | I97Y, F98D, D99Y | −105.98 |
| Variant 3 (ProAgio) | D99N, I102V, Q103I E104I, E83T, T9V, W10Q, G11M, A12K | −115.19 |

[a]Intermolecular Energy ($\Delta E$) = E(Variant) − E(Wild) 200 solutions were ranked according to intermolecular energy. The lowest energy structures of each system were selected to compute the difference of energy.

FIG. 2

| Integrin | Kd(M) |
|---|---|
| αVβ3 | $1.2 \times 10^{-10}$ |
| α1β1 | $2.4 \times 10^{-7}$ |
| αIIbβ3 | $0.9 \times 10^{-7}$ |

BS2G

Spacer Arm: 7.7 Å

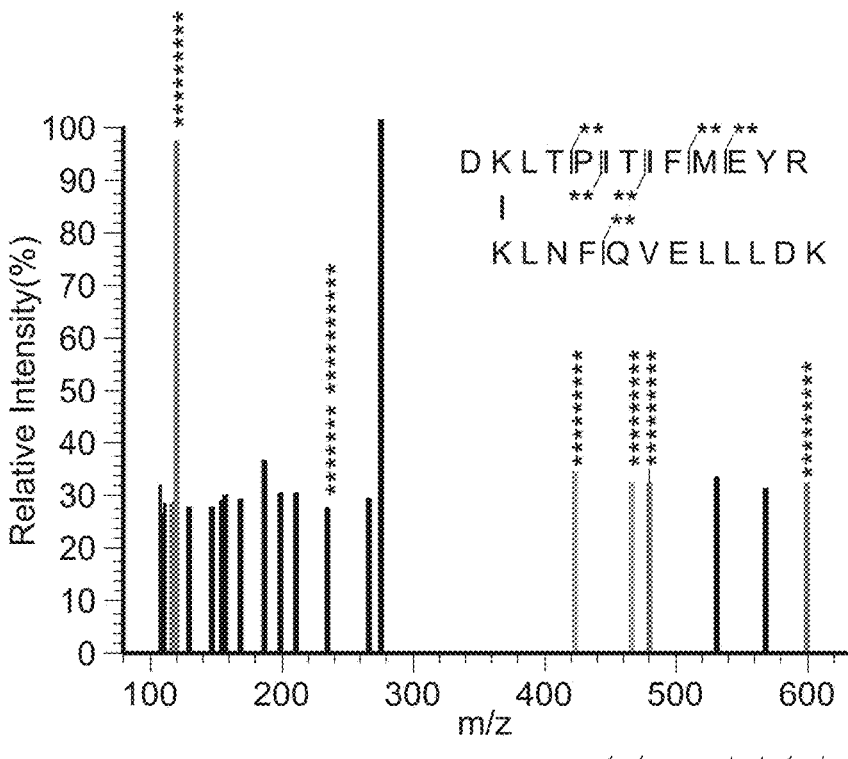
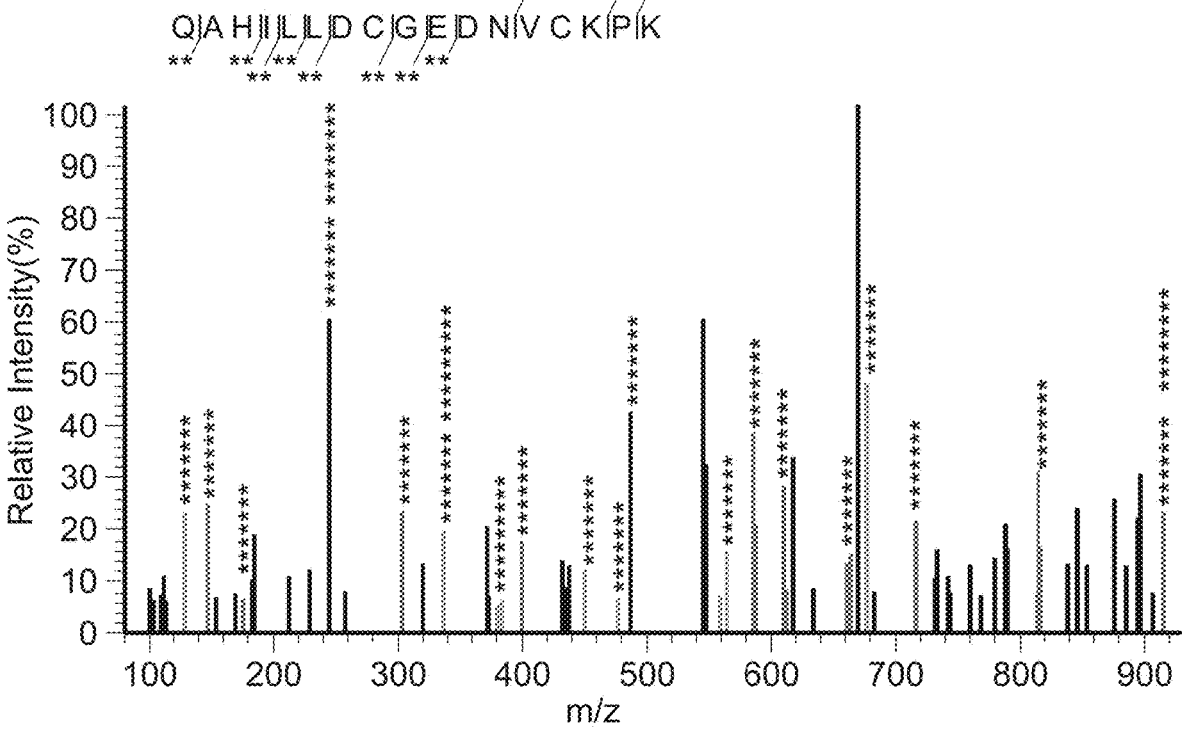
FIG. 13C

Glutaraldehyde

Spacer Arm: 3.1 Å

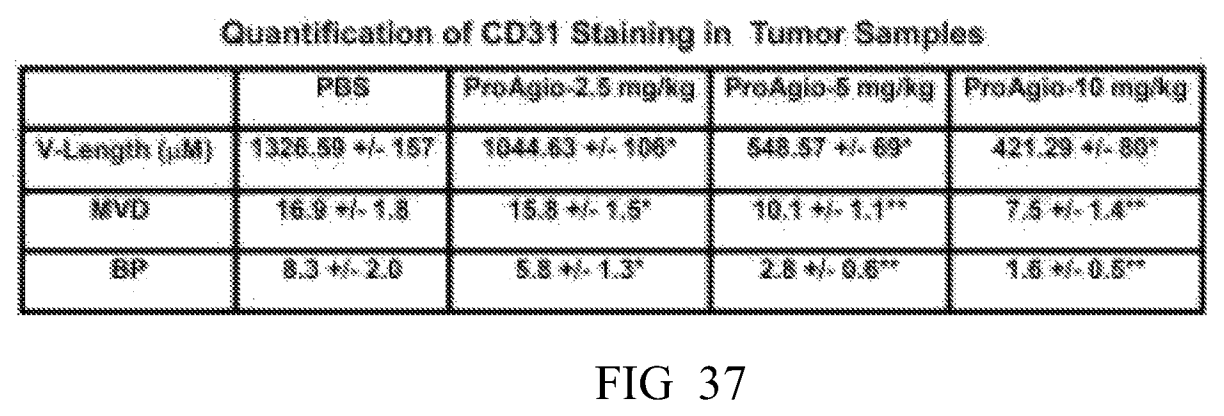

Quantification of CD31 Staining in Tumor Samples

| | PBS | ProAgio-2.5 mg/kg | ProAgio-5 mg/kg | ProAgio-10 mg/kg |
|---|---|---|---|---|
| V.Length (μM) | 1328.59 +/- 197 | 1044.83 +/- 108* | 548.57 +/- 69* | 421.29 +/- 88* |
| MVD | 16.9 +/- 1.9 | 15.3 +/- 1.5* | 10.1 +/- 1.1** | 7.3 +/- 1.4* |
| BP | 8.3 +/- 2.0 | 5.8 +/- 1.3* | 2.8 +/- 0.6** | 1.8 +/- 0.5* |

FIG 37

ProAgio

Buffer

Liver weight after treatments

| Groups | Weight (g, N=10) | | |
|---|---|---|---|
| | Mean | SD | P* |
| TAA + Buffer | 2.21 | 0.21 | 0.07 |
| TAA + ProAgio | 1.79 | 0.16 | |

TIMP1 levels in liver extracts after treatments

| Groups | TIMP1 (ng/g liver) (N=10) | | |
|---|---|---|---|
| | Mean | SD | P* |
| TAA + Buffer | 12920.4 | 3331.2 | 0.0012 |
| TAA + ProAgio | 1762.1 | 899.7 | |

FIG. 49

HepG human liver cancer cells and LX-2 immortalized
activated human hepatic stellate cells

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: An amino acid sequence in integrin Alpha.

<400> SEQUENCE: 1

Thr Glu Met Lys Gln Glu Arg
1               5

<210> SEQ ID NO 2
<211> LENGTH: 8
<212> TYPE: PRT
<213> ORGANISM: Artificial Sequence
<220> FEATURE:
<223> OTHER INFORMATION: An amino acid sequence in integrin Beta.

<400> SEQUENCE: 2

Phe Asn Glu Glu Val Lys Lys Gln
1               5

<210> SEQ ID NO 3
<211> LENGTH: 105
<212> TYPE: PRT
<213> ORGANISM: Artificial Sequence
<220> FEATURE:
<223> OTHER INFORMATION: Amino Acid sequence of wild-type D1-CD2.

<400> SEQUENCE: 3

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg
                100                 105

<210> SEQ ID NO 4
<211> LENGTH: 105
<212> TYPE: PRT
<213> ORGANISM: Artificial Sequence
<220> FEATURE:
```

<223> OTHER INFORMATION: A variant of wild-type D1-CD2.

<400> SEQUENCE: 4

```
Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Asn Asp Val
                85                  90                  95

Cys Asn Phe Ala Ser Arg Gln Glu Arg
            100                 105
```

<210> SEQ ID NO 5
<211> LENGTH: 105
<212> TYPE: PRT
<213> ORGANISM: Artificial Sequence
<220> FEATURE:
<223> OTHER INFORMATION: Another variant of wild-type D1-CD2.

<400> SEQUENCE: 5

```
Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Tyr Asp Tyr Leu Lys Ile Gln Glu Arg
            100                 105
```

<210> SEQ ID NO 6
<211> LENGTH: 8
<212> TYPE: PRT
<213> ORGANISM: Artificial Sequence
<220> FEATURE:
<223> OTHER INFORMATION: An amino acid sequence in wild-type D1-CD2.

<400> SEQUENCE: 6

```
Trp Glu Lys Thr Ser Asp Lys Lys
1               5
```

<210> SEQ ID NO 7
<211> LENGTH: 6
<212> TYPE: PRT
<213> ORGANISM: Artificial Sequence
<220> FEATURE:
<223> OTHER INFORMATION: An amino acid squence from a variant of
      wild-type D1-CD2 capable of crosslinking with integrin Beta 3.

-continued

```
<400> SEQUENCE: 7

Asn Leu Lys Val Ile Ile
1               5
```

INTEGRIN-TARGETING PROTEIN AND METHODS OF USE THEREOF

RELATED APPLICATIONS

This application is a U.S. National Stage Entry of International Patent Application No. PCT/US16/21037, filed on Mar. 4, 2016, which claims the benefit of priority to U.S. Provisional Patent Application 62/129,499, filed Mar. 6, 2015, which is incorporated herein by this reference in its entirety.

FIELD OF TECHNOLOGY

The present application relates to compounds or proteins that may be useful in the treatment of medical conditions associated with fibrosis. The present disclosure relates generally to a polypeptide that binds specifically integrin $\alpha_v\beta_3$. The present disclosure further relates to a method of using the polypeptide for reducing angiogenesis, cell proliferation and fibrosis, and for treating cancer, portal hypertension, and fibrosis related diseases and conditions.

BACKGROUND

Typically, solid tumors are incapable of growing beyond 3-4 mm in diameter without building up their own blood supply. Thus, the establishment of tumor blood vessels is essential for cancer metastasis.

Anti-angiogenic drugs, such as AVASTIN, have been produced that inhibit angiogenesis of solid tumors. However, clinical studies have indicated that the patient survival benefits from these anti-angiogenic drugs have been insignificant. Furthermore, development of anti-angiogenesis drugs has mainly been focused on strategies of blocking VEGF/VEGFR signaling or other RTK pathways that play roles in promoting endothelial cell proliferation and migration.

Integrins are heterodimeric, i.e., combinations of different a and β subunits, cell surface receptors. Integrins not only play a critical role for cell adhesion to the extracellular matrix ("ECM"), but also function as an inside-out and outside-in bidirectional signaling molecule that allows cell activation in response to many biological cues. Integrin $\alpha_v\beta_3$ have unique expression patterns and functionality in angiogenic endothelial cells. Nevertheless, most current approaches in development of therapeutics focus on integrin ligand-binding. Limitations in targeting site(s) and mechanism(s) of action impedes the success of drug development of these therapeutics.

SUMMARY

The present disclosure provides a protein that inhibits angiogenesis of cells without targeting integrin ligand-binding, specifically without targeting VEGF/VEGFR or any other RTK pathways. An aspect of the present disclosure relates to an anti-angiogenic protein that binds to a novel site of integrins $\alpha_v\beta_3$, the protein including a variant of D1-CD2.

Another aspect of the present disclosure relates to a method of administering an anti-angiogenic protein that binds to a novel site of integrins $\alpha_v\beta_3$. The method includes administering a therapeutically effective amount of the anti-angiogenic protein, the anti-angiogenic protein including a variant of D1-CD2.

According to a further aspect, the patent invention is directed to a method of decreasing or preventing fibrosis in a subject in need thereof or at risk thereof, said method comprising administering an isolated polypeptide that specifically binds to integrin $\alpha_v\beta_3$ at βA domain in the region of α2 helix, B—C loop and α2-α3 loop.

According to a further aspect, the patent invention is directed to a polypeptide binding specifically to integrins, and a method of decreasing or preventing fibrosis in a subject in need thereof or at risk thereof, said method comprising administering an isolated polypeptide that specifically binds to integrin $\alpha_v\beta_3$ at βA domain in the region of α2 helix, B—C loop and α2-α3 loop to said subject.

As disclosed herein, in some embodiments, the polypeptide that binds specifically to integrins $\alpha_v\beta_3$ includes a variant of domain 1 of cell adhesion protein (D1-CD2) having an amino acid sequence of at least about 75% similar to the sequence of wild-type D1-CD2, wherein the polypeptide specifically binds to integrin $\alpha_v\beta_3$ at βA domain in the region of α2 helix, B—C loop and α2-α3 loop. In some embodiments, the protein-protein dissociation constant is less than about 1 μM. In some embodiments, the amino acid substitution on the variant having a hydrophilicity value ranges from about −2 to about +2 of the original amino acid of the wild-type D1-CD2.

Further, in some embodiments, the present disclosure provides that the variant includes at least one amino acid substitution selected from a group consisting of (original residue: substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gin), (Phe: Leu, Val), (Leu: He, Val), (Lys: Arg), (Met: Leu, Tyr), (Ser: Thr), (Thr: Ser), (Tip: Tyr), (Tyr: Trp, Phe), and (Val: Phe, Leu). In some embodiments, the variant includes at least one amino acid substitution selected from a group consisting of L94N, E95D, K96V, I97C, F98N, D99F, L100A, K101S, and I102R. In a specific embodiment, the variant includes a sequence having substitution of L94N, E95D, K96V, I97C, F98N, D99F, L100A, K101S, and I102R. In some embodiments, the variant includes at least one substitution selected from a group consisting of I97Y, F98D, and D99Y. In a specific embodiment, the variant comprises a sequence having substitutions of I97Y, F98D, and D99Y. In some embodiments, the variant comprises at least one substitution selected from a group consisting of D99N, I102V, Q103I, E104I, EBT, T9V, W10Q, G11M, A12K. In a specific embodiment, the variant comprises a sequence having substitutions of D99N, I102V, Q103I, E104I, EBT, T9V, W10Q, G11M, A12K.

Still further, in some embodiments, the variant has at least one intermolecular interaction with integrins $\alpha_v\beta_3$. In some embodiments, the variant binds to integrins $\alpha_v\beta_3$ at the βA groove. In specific embodiments, the variant is cross-linked to integrin $\alpha_v$ at TEMKQER (SEQ ID NO:1). In specific embodiments, the variant is crossed-linked to integrin $\beta_3$ at FNEEVKKQ (SEQ ID NO: 2). Yet in other specific embodiments, the variant is crossed-linked to integrin $\beta_3$ at FNEEVKKQ (SEQ ID NO:2). In some embodiments, wherein the variant is PEGylated. In some embodiments, the variant is PEGylated with a polyethylene glycol. In one embodiment, the polyethylene glycol is PEG-20 kDa.

In another aspect of the presently disclosed subject matter, a pharmaceutical composition is provided. The composition includes a therapeutically effective amount of a polypeptide as disclosed above. In some embodiments, the pharmaceutical composition further includes a pharmaceutically acceptable carrier.

Yet in another aspect of present disclosure, a method of inducing apoptosis in a subject having or at risk of having a disease associated with apoptosis is provided. The method includes administering a therapeutically effective amount of the pharmaceutical composition as disclosed above.

Still further, another aspect of the presently disclosed subject matter provides method of preventing or decreasing excessive accumulation of fibrous material within the extracellular matrix in injured or damaged tissue of a subject. The method includes the steps of identifying a subject in need thereof, and administering to the subject an isolated polypeptide as described herein that specifically binds to integrin $\alpha_v\beta_3$ at $\beta$A domain in the region of $\alpha$2 helix, B—C loop and $\alpha$2-$\alpha$3 loop, thereby preventing or decreasing excessive accumulation of fibrous material within the extracellular matrix in said tissue of said subject. In some embodiments, the subject has at least one of liver fibrosis, pancreatic fibrosis, breast fibrosis or other types of fibrosis conditions.

In some embodiments, a method is provided for treating a fibrosis disease in a subject having or at risk of having a fibrosis disease. The method includes the step of administering a therapeutically effective amount of the pharmaceutical composition as discussed herein. Non-limiting examples of the fibrosis disease include liver fibrosis and pancreatic fibrosis.

In some embodiments, the present disclosure provides a method of preventing and treating tumor in a subject. The method includes administering a therapeutically effective amount of the pharmaceutical composition as disclosed herein.

In some embodiments, the pharmaceutical composition as disclosed herein is suitable for topical application, injection, oral administration, or time release dosage.

In some embodiments of the presently disclosed subject matter, the subject is a mammal. In some embodiments, the subject is a human.

Still further, in some embodiment, the present disclosure provide an isolated polypeptide that specifically binds to integrin $\alpha_v\beta_3$ at $\beta$A domain in the region of $\alpha$2 helix, B—C loop and $\alpha$2-$\alpha$3 loop. In some embodiments, the $K_D$ of the specific binding is less than about 1 $\mu$M. In other embodiments, the $K_D$ of the specific binding is between $10^{-8}$ and $10^{-9}$ M.

Definitions

The term "angiogenesis" is defined as the formation of new vasculature which benefits tissue perfusion. This includes the formation of new vessels by sprouting of endothelial cells from existing blood vessels or the remodeling of existing vessels to alter size, maturity direction or flow properties to improve blood perfusion of tissue.

The terms "subject," "individual," "patient," and "host" are used interchangeably herein and refer to any vertebrate, particularly any mammal, and most particularly including human subjects, farm animals, and mammalian pets. The subject may be, but is not necessarily, under the care of a health care professional such as a doctor or veterinarian and may be in need of therapeutic treatment with the compositions of the disclosure.

The term "fibrotic" diseases, disorders, or conditions include those mentioned herein, and further include acute and chronic, clinical or sub-clinical presentation, in which fibrogenic associated biology or pathology is evident. Fibrotic diseases, disorders, or conditions include diseases, disorders or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. Fibrotic diseases, disorders, or conditions include, for example, fibrogenic-related biology or pathology characterized by fibrosis.

The term "therapeutically effective amount," as used herein, refers to the amount of a composition containing a modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depends conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

The term "vector" as used herein means a DNA molecule serving as a vehicle capable of stably carrying exogenous genes into host cells. For useful application, a vector should be replicable, have a system for introducing itself into a host cell, and possess selectable markers.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, by way of example only, an alpha-carbon that is bound to a hydrogen, a carboxyl group, an amino group, and an R-group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, and methionine methyl sulfonium.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By way of example, an agent or a compound being administered includes, but is not limited to, a natural amino acid polypeptide, non-natural amino acid polypeptide, modified natural amino acid polypeptide, or modified non-amino acid polypeptide. Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments. An appropriate "effective" amount in any individual case may be determined using techniques, such as a dose escalation study.

The term "cell or population of cells" as used herein refers to an isolated cell or plurality of cells excised from a tissue or grown in vitro by tissue culture techniques. Most particularly, a population of cells refers to cells in vivo in a tissue of an animal or human.

The term "contacting a cell or population of cells" as used herein refers to delivering a peptide or probe according to the present disclosure to an isolated or cultured cell or population of cells or administering the probe in a suitable pharmaceutically acceptable carrier to the target tissue of an animal or human. Administration may be, but is not limited to, intravenous delivery, intraperitoneal delivery, intramuscularly, subcutaneously, or by any other method known in the art. One advantageous method is to deliver directly into a blood vessel leading immediately into a target organ or tissue such as a pancreas, thereby reducing dilution of the probe in the general circulatory system.

The term "pharmaceutically acceptable carrier" as used herein refers to a diluent, adjuvant, excipient, or vehicle with which a heterodimeric probe of the disclosure is administered and which is approved by a regulatory agency of the federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol, and the like. The present compositions, if desired, can also contain minor amounts of wetting or emulsifying agents, or pH buffering agents. The present compositions advantageously may take the form of solutions, emulsion, sustained-release formulations, or any other form suitable for use.

The terms "polypeptide," "peptide," and "protein" are used interchangeably herein to refer to a polymer of amino acid residues.

The term "variant" refers to a peptide or polynucleotide that differs from a reference peptide or polynucleotide, but retains essential properties. A typical variant of a peptide differs in amino acid sequence from another, reference peptide. Generally, differences are limited so that the sequences of the reference peptide and the variant are closely similar overall and, in many regions, identical. A variant and reference peptide may differ in amino acid sequence by one or more modifications (e.g., substitutions, additions, and/or deletions). A variant of a peptide includes conservatively modified variants (e.g., conservative variant of about 75%, about 80%, about 85%, about 90%, about 95%, about 98%, and about 99%) of the original sequence. A substituted or inserted amino acid residue may or may not be one encoded by the genetic code. A variant of a peptide may be naturally occurring, such as an allelic variant, or it may be a variant that is not known to occur naturally.

The term "target" as used herein refers to a peptide, cell, tissue, tumor, etc., for which it is desired to detect. The target peptide may be on a cell surface, the cell being isolated from an animal host, a cultured cell, or a cell or population of cells in a tissue of an animal.

The present disclosure includes peptides which are derivable from the naturally occurring sequence of the peptide. A peptide is said to be "derivable from a naturally occurring amino acid sequence" if it can be obtained by fragmenting a naturally occurring sequence, or if it can be synthesized based upon knowledge of the sequence of the naturally occurring amino acid sequence or of the genetic material (DNA or RNA) that encodes this sequence. Included within the scope of the present disclosure are those molecules which are said to be "derivatives" of a peptide. Such a "derivative" or "variant" shares substantial similarity with the peptide or a similarly sized fragment of the peptide and is capable of functioning with the same biological activity as the peptide.

The terms "binds specifically" or "specifically binding" as used herein refers to the binding of a binding protein to a predetermined protein (e.g. integrins). The affinity of the binding is defined in terms of a dissociation constant ($K_D$). The binding protein specifically binds an protein when the $K_D$ is less than about 10.sup.-7 M, such as about 10.sup.-8 M or less, such as about 10.sup.-9 M or less, about 10.sup.-10 M or less; about 10.sup.-11 M or less, about 10.sup.-12 M or less, or even less, and binds to the predetermined protein with an affinity corresponding to a $K_D$ that is at least ten-fold lower than its affinity for binding to a non-specific antigen (such as BSA), such as at least 100 fold lower, for instance at least 1,000 fold lower, such as at least 10,000 fold lower. The term "$K_D$" or "$K_D$", as used herein, refers to the dissociation constant of a particular protein-protein binding interaction as is known in the art.

The derivatives of the present disclosure include fragments which, in addition to containing a sequence that is substantially similar to that of a naturally occurring peptide may contain one or more additional amino acids at their amino and/or their carboxy termini. Similarly, the disclosure includes peptide fragments which, although containing a sequence that is substantially similar to that of a naturally occurring peptide, may lack one or more additional amino acids at their amino and/or their carboxy termini that are naturally found on the peptide.

The term "prophylactically effective amount," as used herein, refers an amount of a composition containing at least one non-natural amino acid polypeptide or at least one modified non-natural amino acid polypeptide prophylactically applied to a patient which will relieve to some extent one or more of the symptoms of a disease, condition, or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The phrase "substantially similar," in the context of two nucleic acids or polypeptides, refers to two or more sequences or subsequences that have at least 75%, preferably at least 85%), more preferably at least 90%, 95% or higher, or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40-60 residues in length or any integral value there between, preferably over a longer region than 60-80 residues, more preferably at least about 90-100 residues, and most preferably the sequences are substantially identical over the full length of the sequences being compared, such as the coding region of a nucleotide sequence for example.

The term "synergistic", as used herein, refers to a combination of prophylactic or therapeutic effective agents which is more effective than the additive effects of any two or more single agents. A synergistic effect of a combination of prophylactic or therapeutic agents may permit the use of lower dosages of one or more of the agents and/or less frequent administration of the agents to a subject with a specific disease or condition. In some cases, a synergistic effect of a combination of prophylactic or therapeutic agents may be used to avoid or reduce adverse or unwanted side effects associated with the use of any single therapy.

The term "therapeutically effective amount," as used herein, refers to the amount of a composition containing at least one non-natural amino acid polypeptide and/or at least one modified non-natural amino acid polypeptide administered to a patient already suffering from a disease, condition, or disorder, sufficient to cure or at least partially arrest, or relieve to some extent one or more of the symptoms of the disease, disorder, or condition being treated. The effectiveness of such compositions depend upon conditions including, but not limited to, the severity and course of the disease, disorder, or condition, previous therapy, the patient's health status and response to the drugs, and the judgment of the treating physician. By way of example only, therapeutically effective amounts may be determined by routine experimentation, including but not limited to a dose escalation clinical trial.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide.

As used herein, the term "subject" refers to a target of administration of the pharmaceutical composition. The subject of the herein disclosed methods can be a vertebrate, such as a mammal, a fish, a bird, a reptile, or an amphibian. Thus, the subject of the herein disclosed methods can be a human or non-human. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex.

The disclosure also encompasses the obvious or trivial variants of the above-described fragments which have inconsequential amino acid substitutions (and thus have amino acid sequences which differ from that of the natural sequence) provided that such variants have an activity which is substantially identical to that of the above-described derivatives. Examples of obvious or trivial substitutions include the substitution of one basic residue for another (i.e. Arg for Lys), the substitution of one hydrophobic residue for another (i.e. Leu for He), or the substitution of one aromatic residue for another (i.e. Phe for Tyr), etc.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 2 is a tabular representation illustrating intermolecular energies of D1-CD2 variants according to the present disclosure.

FIG. 13C illustrates the crosslinking of ProAgio using Bis(Sulfosuccinimidyl)-glutarate according to the present disclosure.

FIG. 37 is a tabular representation illustrating the effects of ProAgio-PEG on tumor vessels according to the present disclosure.

FIG. 49 is a tabular representation illustrating the effects of ProAgio on livers from fibrosis mice according to the present disclosure.

DETAILED DESCRIPTION

Figures 1A, 1B, 1C, 1D:
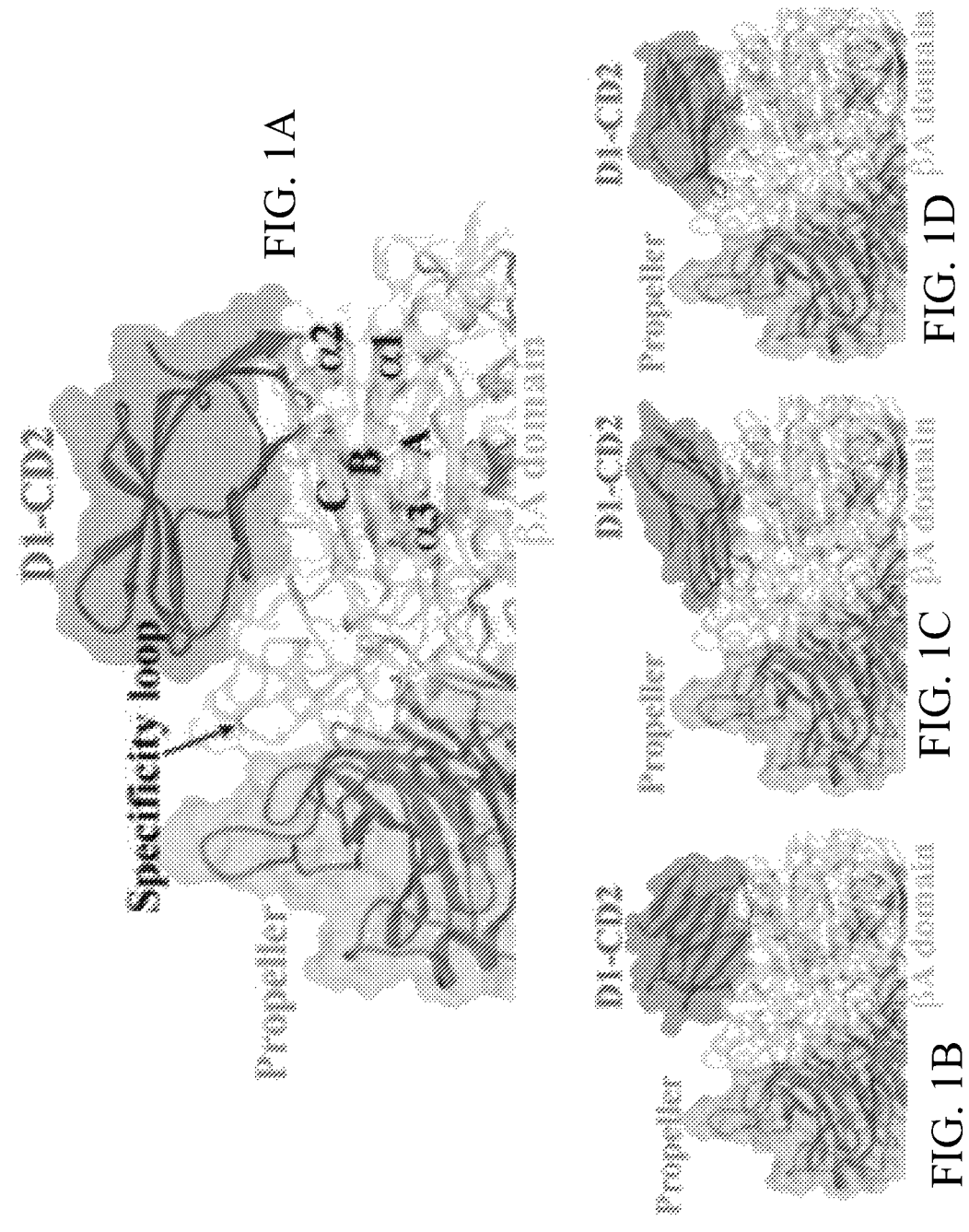
FIG. 1A is a rendering of D1-CD2 docking into the βA groove according to the present disclosure.
FIG. 1B is a rendering of D1-CD2 docking into the βA groove according to the present disclosure.
FIG. 1C is a rendering of D1-CD2 docking into the βA groove according to the present disclosure.
FIG. 1D is a rendering of D1-CD2 docking into the βA groove according to the present disclosure.
Figure 3:
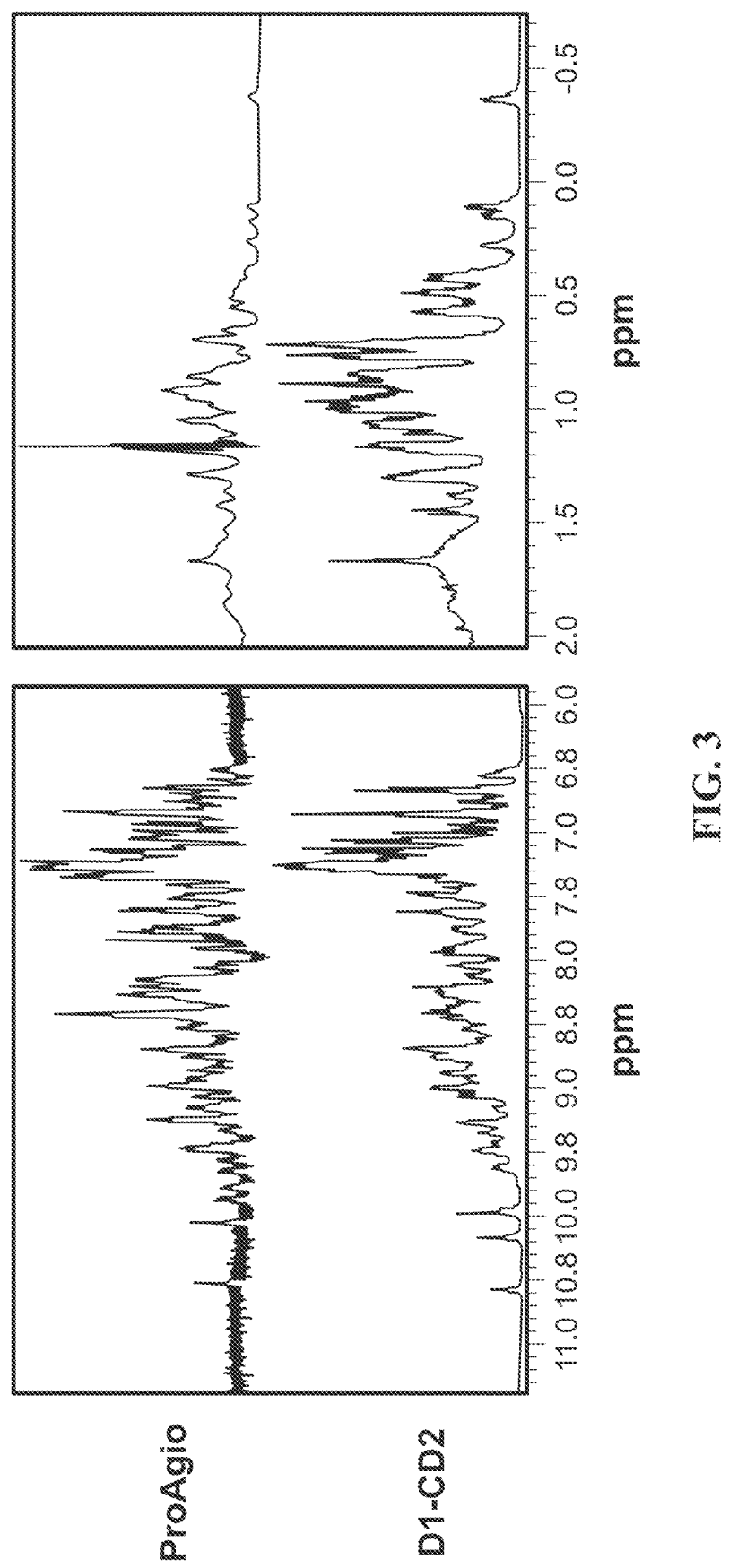
FIG. 3 illustrates H-NMR readouts depicting ProAgio having similar structural properties to those of D1-CD2 according to the present disclosure.
Figure 4A:
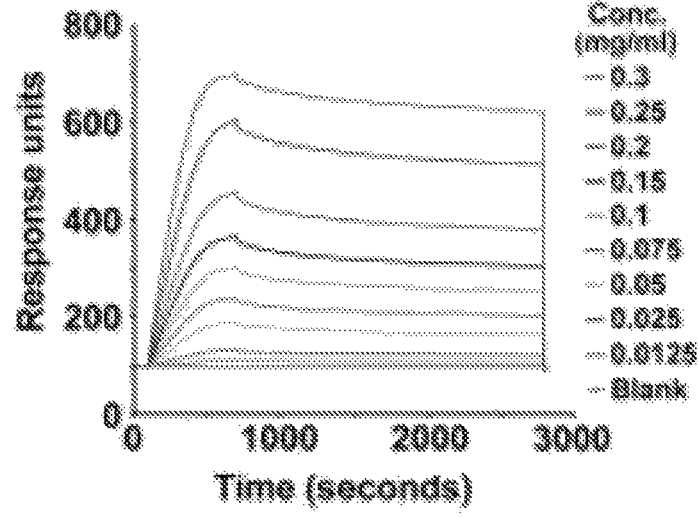
FIG. 4A is a graphical representation illustrating ProAgio interactions with integrin according to the present disclosure.
Figure 4B:
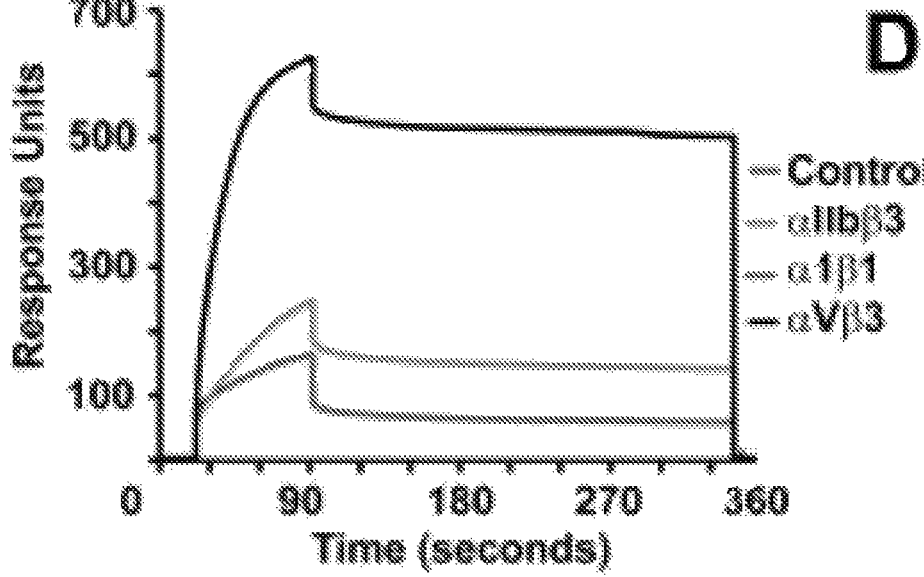
FIG. 4B is a graphical representation illustrating ProAgio interactions with integrin according to the present disclosure.
Figures 4C, 5:
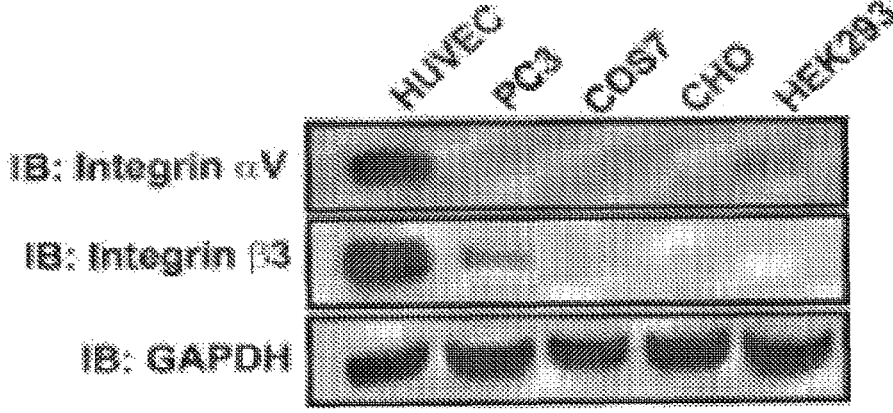
FIG. 4C is a tabular representation illustrating ProAgio interactions with integrin according to the present disclosure.
FIG. 5 illustrates the $\alpha_v\beta_3$ expression of HUVEC cells according to the present disclosure.
Figure 6:
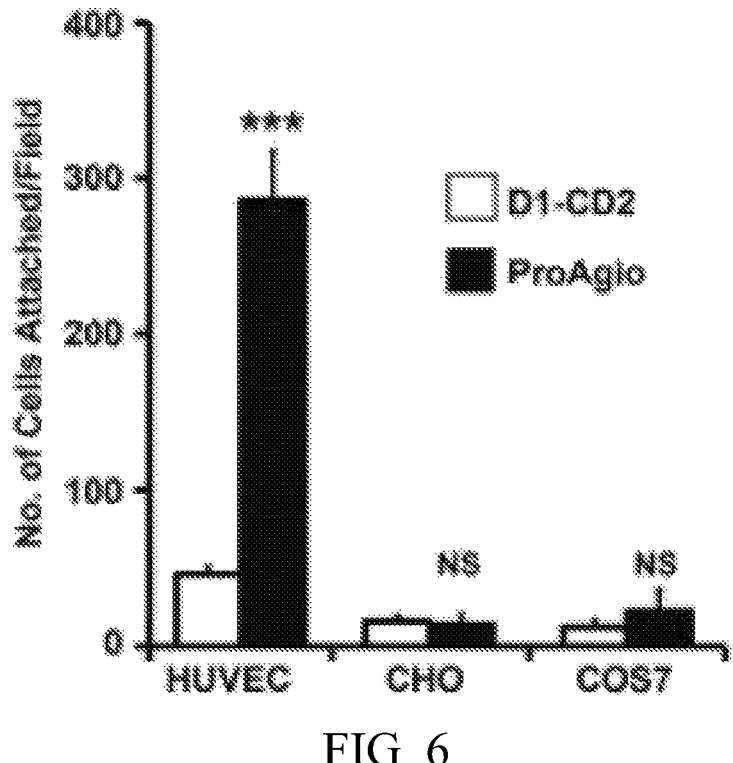
FIG. 6 is a graphical representation illustrating the attachment of HUVEC cells to ProAgio according to the present disclosure.
Figure 7:
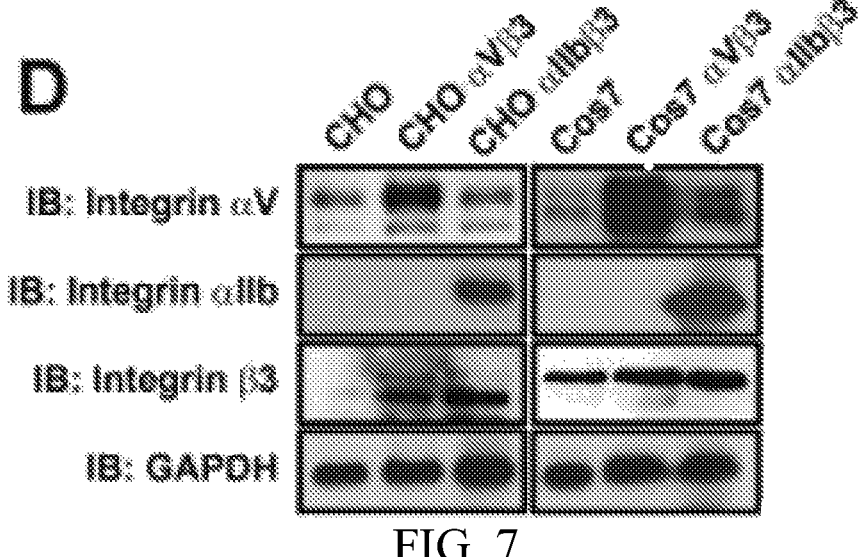
FIG. 7 illustrates exogenous $\alpha_v\beta_3$ expression in CHO and COS-7 cells according to the present disclosure.
Figure 8:
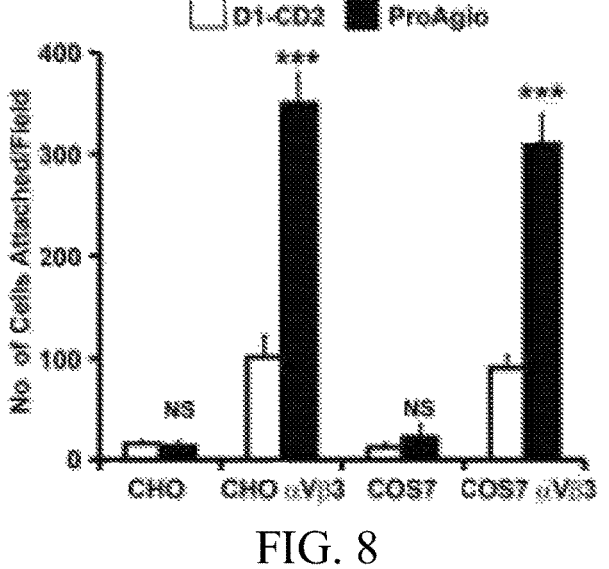
FIG. 8 is a graphical representation illustrating attachment of the $\alpha_v\beta_3$ expressing CHO and COS-7 cells to ProAgio coated plates according to the present disclosure.
Figure 9:
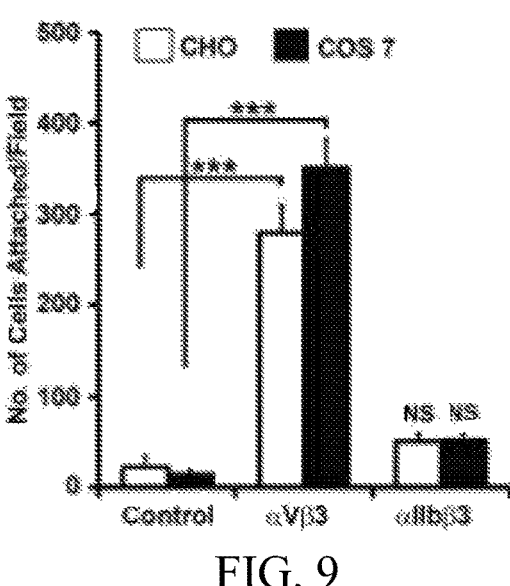
FIG. 9 is a graphical representation illustrating the lack of attachment of integrin $\alpha_v\beta_3$ expressing CHO cells to ProAgio coated plates according to the present disclosure.

This disclosure provides an anti-angiogenic or anti-fibrotic agent and a method of inhibiting angiogenesis in which the angiogenic or fibrosis dependent condition in a mammal is treated by the administering an anti-angiogenic agent, termed ProAgio to the mammal, in a therapeutically effective amount and frequency to produce a regression or arrest of the condition without significant toxicity. The angiogenic dependent condition may be selected from the group consisting of neoplasm, including a solid tumor neoplasm, including breast carcinoma, lung carcinoma, prostate carcinoma, colon carcinoma, prostate carcinoma, ovarian carcinoma, neuroblastoma, central nervous system tumor, neuroblastoma, glioblastoma multiforme or melanoma. While no list can be complete, the anti-angiogenic agent may be used to produce a regression or arrest of most, if not all, solid tumors. The mammal receiving the treatment can be a human.

This disclosure relates generally to a polypeptide that binds specifically integrin $\alpha_v\beta_3$. More particularly, the present disclosure relates to a variant of domain 1 of cell adhesion protein (D1-CD2) that has an amino acid sequence at least about 75% similar to the sequence of wild-type D1-CD2 1 KEITNALETWGALGQDINLDIPSFQMSDDIDDIK-WEKTSDKKKIAQFRKEKETFKEKD TYKLFKNGTLKIKHLKTDDQDIYKVSIYDTKGKNV-LEKIFDLKIQER 106 (SEQ ID NO:3). This disclosure further relates to a method of using the polypeptide in treating angiogenesis, cell proliferation, cancer, and fibrosis related diseases and conditions. This disclosure also includes an isolated polypeptide that specifically binds to integrin $\alpha_v\beta_3$ at $\beta$A domain in the region of $\alpha$2 helix, B—C loop and $\alpha$2-$\alpha$3 loop. An example of such a polypeptide is ProAgio. Exemplary sequences of ProAgio include KEITNALETWGALGQDINLDIPSFQMSDDIDDIK-WEKTSDKKKIAQFRKEKETFKEKD TYKLFKNGTLKIKHLKTDDQDIYKVSIYDTKGKNV-NDVCNFASRQER (SEQ ID NO:4) and KEITNALETWGALGQDINLDIPSFQMSDDIDDIK-WEKTSDKKKIAQFRKEKETFKEKD TYKLFKNGTLKIKHLKTDDQDIYKVSIYDTKGKNV-LEKYDYLKIQER (SEQ ID NO: 5)

ProAgio, as disclosed herein, includes a host protein and domain 1 of cell adhesion protein CD2 ("D1 CD2"). ProAgio targets integrin $\alpha_v\beta_3$, at a novel site, i.e., a groove in the region of $\alpha$2 helix, B—C loop and $\alpha$2-$\alpha$3 loop (the "$\beta$A groove"). The $\beta$A groove is present in nearly all other $\beta$ integrins, and is relatively close to the RGD binding site in the $\beta$A domain. Thus, while it is disclosed that ProAgio may target the $\beta$A groove of integrin $\alpha_v\beta_3$, one skilled in the art should appreciate that ProAgio may be used to target the $\beta$A groove of any $\beta$ integrin containing the $\beta$A groove.

One embodiment includes a method of preventing or decreasing excessive accumulation of fibrous material within the extracellular matrix in injured or damaged tissue of a subject comprising identifying a subject in need thereof, and administering to the subject a polypeptide that binds specifically to integrins $\alpha_v\beta_3$, comprising: a variant of domain 1 of cell adhesion protein (D1-CD2) having an amino acid sequence of at least about 75% similar to the sequence of wild-type D1-CD2, wherein the polypeptide specifically binds to integrin $\alpha_v\beta_3$ at $\beta$A domain in the region of $\alpha$2 helix, B—C loop and $\alpha$2-$\alpha$3 loop. The subject may have pancreatic fibrosis, liver fibrosis, or breast fibrosis.

Exemplary fibrotic diseases, disorders and conditions include, for example, scleroderma (including morphea, generalized morphea, or linear scleroderma), kidney fibrosis (including glomerular sclerosis, renal tubulointerstitial fibrosis, progressive renal disease or diabetic nephropathy), cardiac fibrosis (e.g. myocardial fibrosis), pulmonary fibrosis (e.g., glomerulosclerosis pulmonary fibrosis, idiopathic pulmonary fibrosis, silicosis, asbestosis, interstitial lung disease, interstitial fibrotic lung disease, and chemotherapy/ radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myeloid leukemia, acute myelogenous leukemia, myelodysplastic syndrome, myeloproferative syndrome, gynecological cancer, Kaposi's sarcoma, Hansen's disease, collagenous colitis and acute fibrosis. Fibrosis can be either chronic or acute. Fibrotic conditions include excessive amounts of fibrous tissue, including excessive amounts of extracellular matrix accumulation within a tissue, forming tissue which causes dysfunction and, potentially, organ failure.

This disclosure includes non-toxic proteins, hereinafter referred to as ProAgio, that inhibit tumor growth and exhibits activity in induction of angiogenic endothelial cell apoptosis without targeting VEGF/VEGFR or any other RTK pathways.

Without being bound to a single theory, it is contemplated that ProAgio specifically induces apoptosis of integrin $\alpha_v\beta_3$ expressing cells with high efficacy by recruiting and activating caspase 8 at cytoplasmic domain of $\beta$3. Since both cancers associated pancreatic stellate cells (CAPaSC) and angiogenic endothelial cells express high levels of integrin $\alpha_v\beta_3$, ProAgio likely depletes CAPaSC and eliminates new blood vessels in and around tumors or other tissues.

ProAgio induces apoptosis with or without ligand binding, and ProAgio binding does not interfere with RGD binding, thereby suggesting the effects of ProAgio are independent of ligand-binding. ProAgio induces cell apoptosis through integrin $\alpha_v\beta_3$ via a mechanism different from anoikis. Thus, ProAgio does not necessarily compete with strong integrin-ligand interactions, and does not need to induce anoikis, which may not occur due to angiogenic endothelial cell-to-ECM adhesions involving interactions between multiple pairs of integrin and multiple types of ECM.

One embodiment includes proteins capable of inducing apoptosis of activated hepatic and pancreatic stellate cells and myofibroblast, which are believed to be a major source of extracellular matrix in the liver and other organs. Stellate cells and myofibroblasts respond to a variety of growth factors and cytokines present in the liver and other organs, some of which they also produce liver fibrosis. The apoptosis induction of stellate cell, promotion of matrix degradation, or promotion of stellate cell apoptosis reduces liver fibrosis. In liver activated hepatic stellar cells, dedifferentiated sinusoidal endothelial cells (LSEC) have high level of integrin $\alpha_v\beta_3$. The effect of ProAgio killing the dedifferentiated LSEC reduces portal hypertension.

Modifications and changes can be made in the structure of the peptides of this disclosure and still obtain a molecule having similar characteristics as the peptide (e.g., a conservative amino acid substitution). For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a peptide with like properties.

FIGS. 1A through 19 illustrate the designing of ProAgio to bind to the βA groove. While ProAgio described herein is capable of binding to the βA groove of integrin $\alpha_v\beta_3$, one skilled in the art should appreciate that ProAgio may bind to any integrin containing the βA groove as described above.

The agent appears to inhibit or prevent angiogenesis by inhibiting or controlling apoptosis and fibrosis The developed polypeptides demonstrated strong activity in the induction of endothelial cell apoptosis without effects on epithelial and fibroblast cells in the in vitro analyses. In addition, the developed polypeptides do not exerted toxicity on already existing normal blood vessels. Survival factors include vascular endothelial cell growth factors or mitogens, as well as those factors which do not appear to have a direct growth-stimulatory effect but allow the cells to recover from injury.

These agents may be incorporated into methods of treating a mammal by inhibiting angiogenesis that include the steps of administering the anti-angiogenic and anti-fibrotic agents. In certain embodiments, the anti-angiogenic or anti-fibrotic polypeptide exhibited extended circulation time compared to small molecules and short peptide agents.

Specific embodiments provide methods of inhibiting angiogenesis or fibrosis and methods of treating angiogenesis-associated or fibrotic diseases. In other embodiments, the present invention provides methods of inhibiting or reducing tumor growth and methods of treating an individual suffering from cancer. These methods involve administering to the individual a therapeutically effective amount of one or more polypeptide therapeutic agents as described above. These methods are particularly aimed at therapeutic and prophylactic treatments of animals, and more particularly, humans.

As described herein, angiogenesis-associated or fibrotic diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, coronary collaterals, ischemic limb angiogenesis, corneal diseases, rubeosis, arthritis, diabetic neovascularization, fractures, vasculogenesis, hematopoiesis.

One potential benefit of the combination of an anti-angiogenic or anti-fibrotic agent and a chemotherapeutic agent may be an improvement in the treatment and control of an angiogenic dependent condition with reduced doses of a chemotherapeutic agent. The combination can be administered for a prolonged period of time, or optionally a shorter duration of treatment may be administered due to the increased effectiveness of the combination.

Depending on the nature of the combinatory therapy, administration of the polypeptide therapeutic agents of the invention may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In silico and in situ analyses indicate proteins capable of binding integrin α.sub.vβ3. Of note, the βA of β3 affects ligand-binding and integrin signaling transmission. D1-CD2 of both human and rat origin) exhibit rather weak affinities for known binding sites of integrin α.sub.vβ3. D1-CD2 docks to several sites of the βA domain, including a novel site, i.e., the BA groove, at various orientations (illustrated in FIGS. 1A-1D). However, due to a lack of strong contacts with residues of the βA groove, docking of D1-CD2 to the βA groove was enhanced by mutating residues of D1-CD2 at contacting positions to better match the corresponding residues in the βA groove. Additional mutations were introduced into D1-CD2 to counter potential structural disturbance by the previously mentioned mutations and to maintain a wild-type β-sheet packing. The energies exhibited by the docking of these D1-CD2 variants on the integrins were substantially increased as compared to un-mutated D1-CD2 (illustrated in FIG. 2). Further, the binding energy fell significantly when the corresponding residues in the integrin were mutated, thereby disrupting the designed contacts.

D1-CD2 variants were expressed in bacterial E. coli and subsequently purified. ProAgio exhibited structural properties similar to those of the parental D1-CD2 protein as demonstrated by H-NMR (illustrated in FIG. 3), far UV-CD, and fluorescent spectra analyses. This indicates ProAgio is beneficially folded. Moreover, biacore binding analyses demonstrate ProAgio interacts with integrin $\alpha_v\beta_3$ with a high affinity. ProAgio also interacts with two other pairs of integrin weakly, suggesting ProAgio specifically interacts with integrin α.sub.vβ3 (illustrated in FIG. 4A-4C).

Cell attachment assays using a culture plate coated with ProAgio verify the ProAgio/integrin $\alpha_v\beta_3$ interaction. HUVEC cells, which have high levels of $\alpha_v\beta_3$ expression (illustrated in FIG. 5), attached strongly to ProAgio coated plates (illustrated in FIG. 6). CHO and COS-7 cells, which do not express $\alpha_v\beta_3$, did not attach to the ProAgio coated plates. $\alpha_v\beta_3$ was also exogenously expressed in CHO and COS-7 cells (illustrated in FIG. 7) and the same aforementioned cell attachment analyses were performed on these cells. The α.sub.vβ3 expressing CHO and COS-7 cells attached to the ProAgio coated plates (illustrated in FIG. 8). As a control, integrin $\alpha_v\beta_3$ expressing CHO cells did not attach to the ProAgio coated plates (illustrated in FIG. 9). These cell attachment assay analyses indicate ProAgio interacts with integrin $\alpha_v\beta_3$ on the cell surface.

Figures 10, 11:
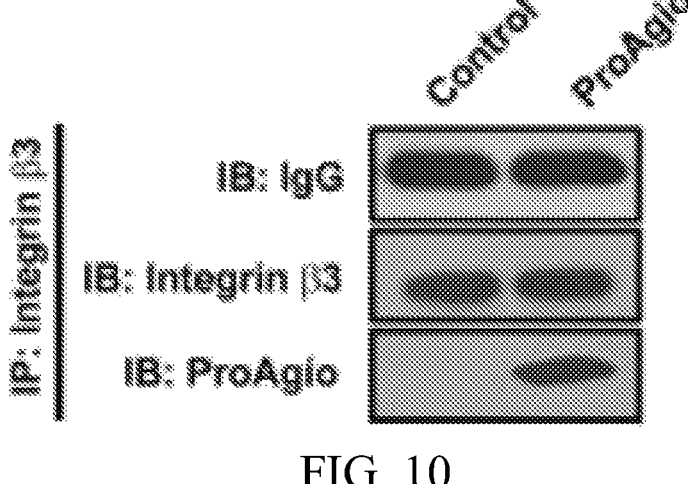
FIG. 10 illustrates co-immunoprecipitation of ProAgio with integrin β3 in HUVEC cell extracts according to the present disclosure.
FIG. 11 is a graphical representation illustrating the binding of RGD does not prevent the HUVEC cells from attaching to ProAgio according to the present disclosure.
Figure 12:
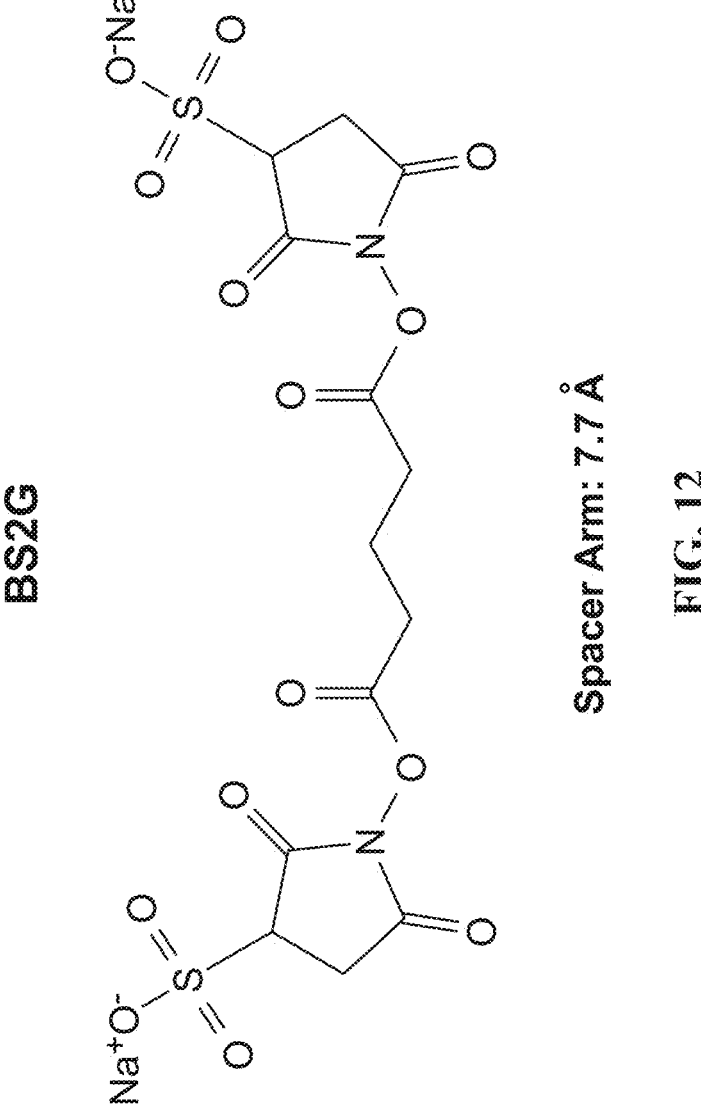
FIG. 12 illustrates confirmation that binding of RGD does not prevent HUVEC cells from attaching to ProAgio according to the present disclosure.

Interaction of ProAgio with the integrin was further verified by co-immunoprecipitation of ProAgio with integrin β3 in HUVEC cell extracts (illustrated in FIG. 10).

Since ProAgio binds to the βA groove, ProAgio-binding does not compete with RGD-binding, since ProAgio and RGD do not bind to the same site. An attachment assay was carried out whereby HUVEC cells were incubated with RGD, and subsequently assayed for the attachment of ProAgio. This experiment evidences the binding of both RGD and ProAgio to the HUVEC cells without hindrance (illustrated in FIG. 11).

Figure 13A:
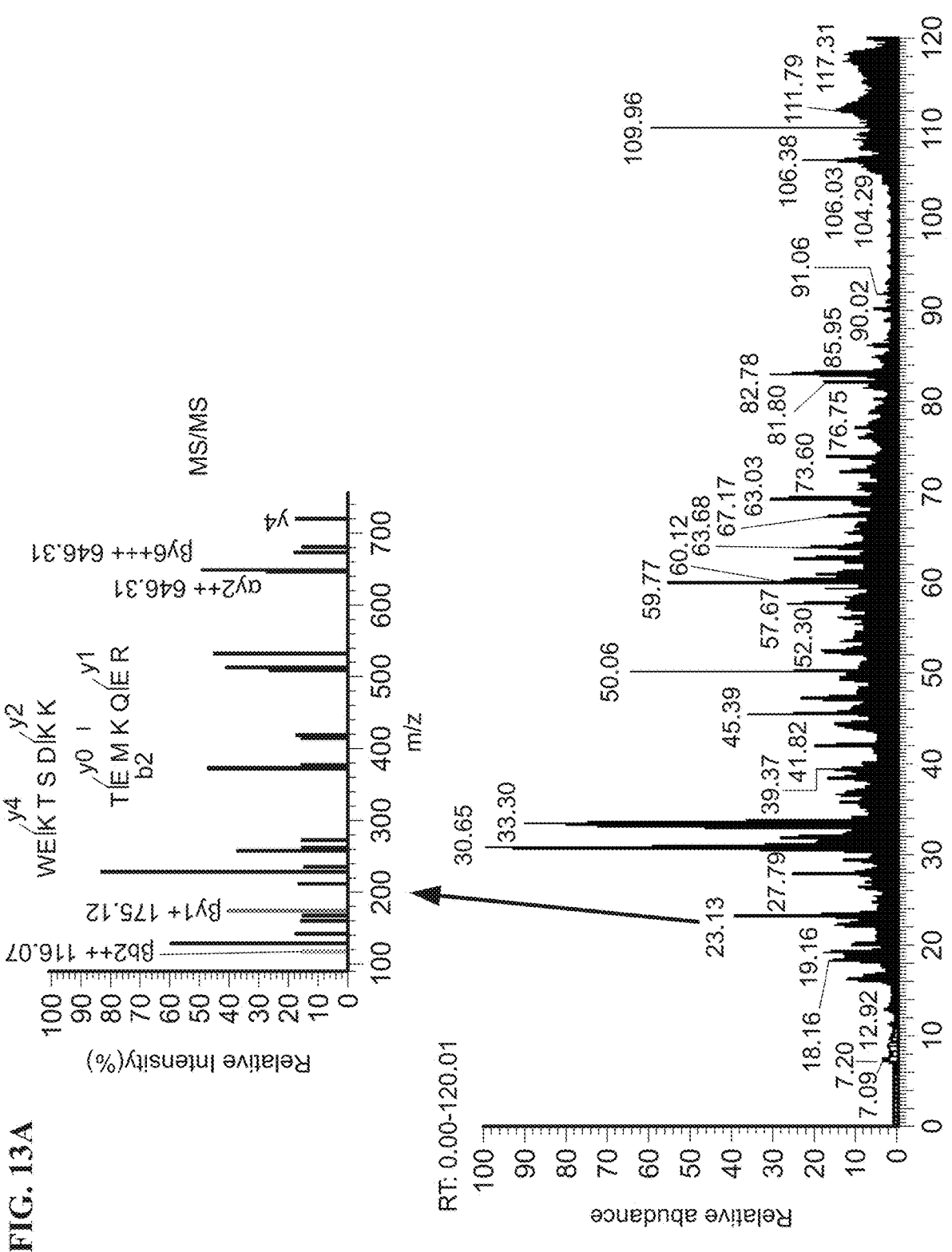
FIG. 13A illustrates the crosslinking of ProAgio to integrin av according to the present disclosure.
Figure 13B:
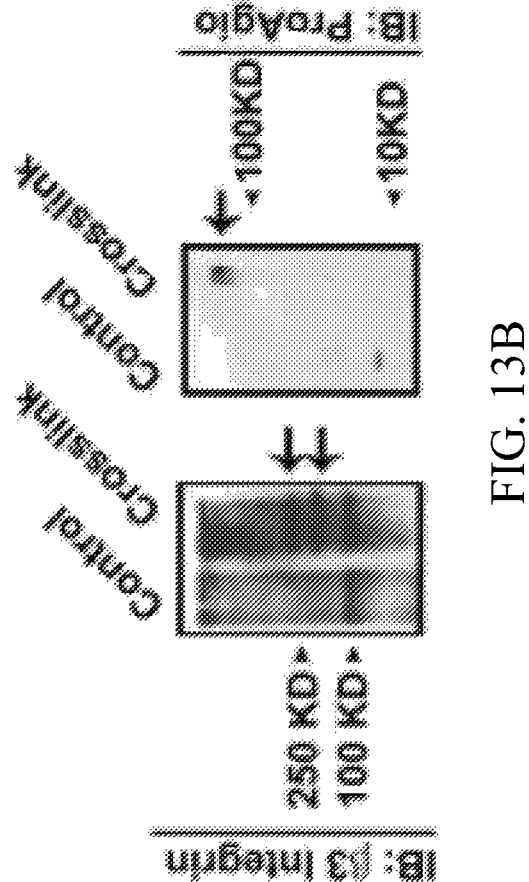
FIG. 13B illustrates the crosslinking of ProAgio to integrin av according to the present disclosure.
Figure 14:
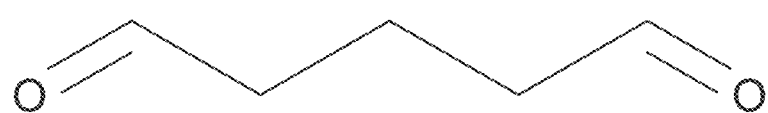
FIG. 14 illustrates the crosslinking ProAgio using glutaraldehyde according to the present disclosure.
Figures 15A, 15B:
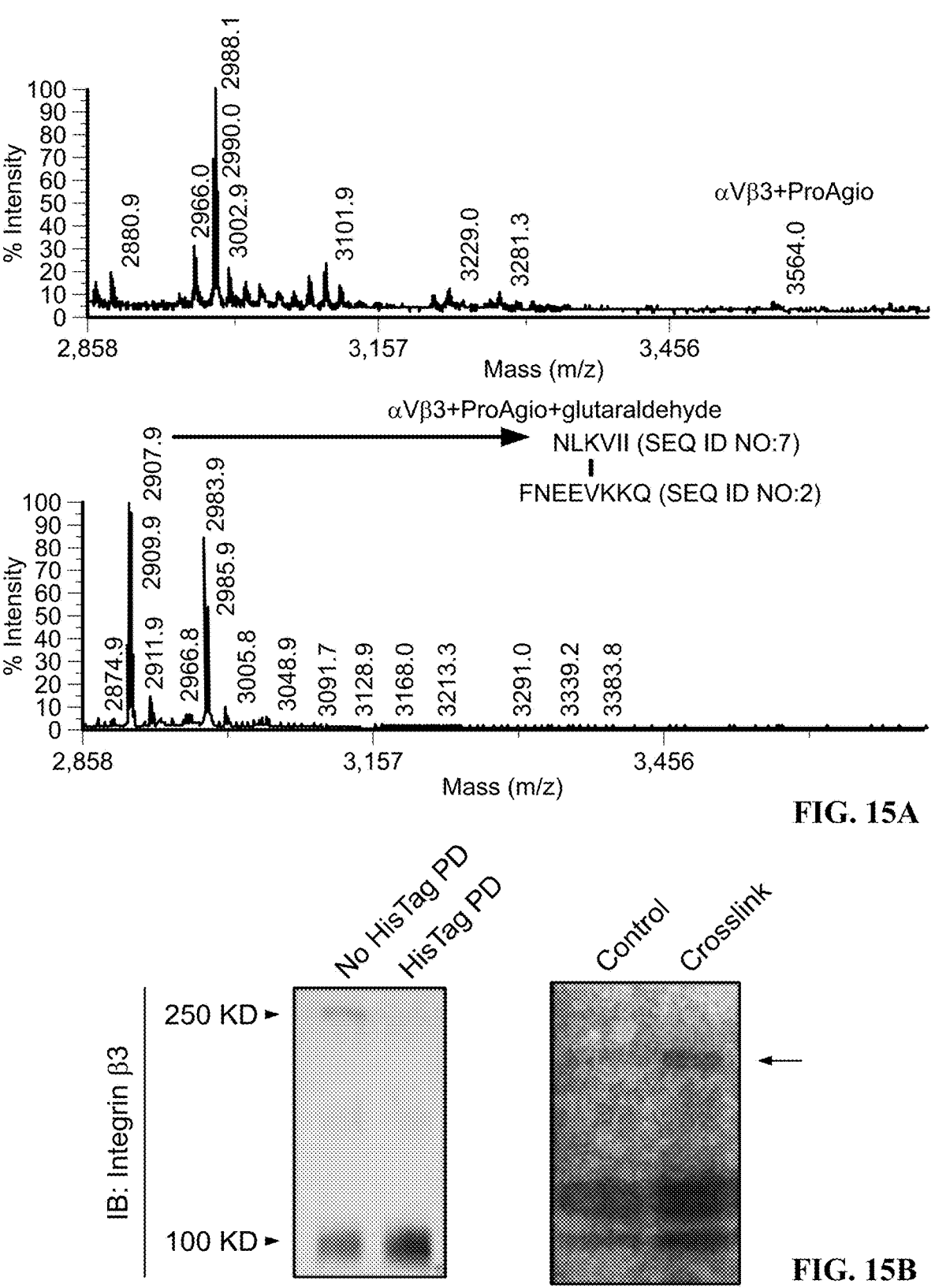
FIG. 15A illustrates the crosslinking ProAgio using glutaraldehyde according to the present disclosure.
FIG. 15B illustrates the crosslinking ProAgio using glutaraldehyde according to the present disclosure.
Figure 16:
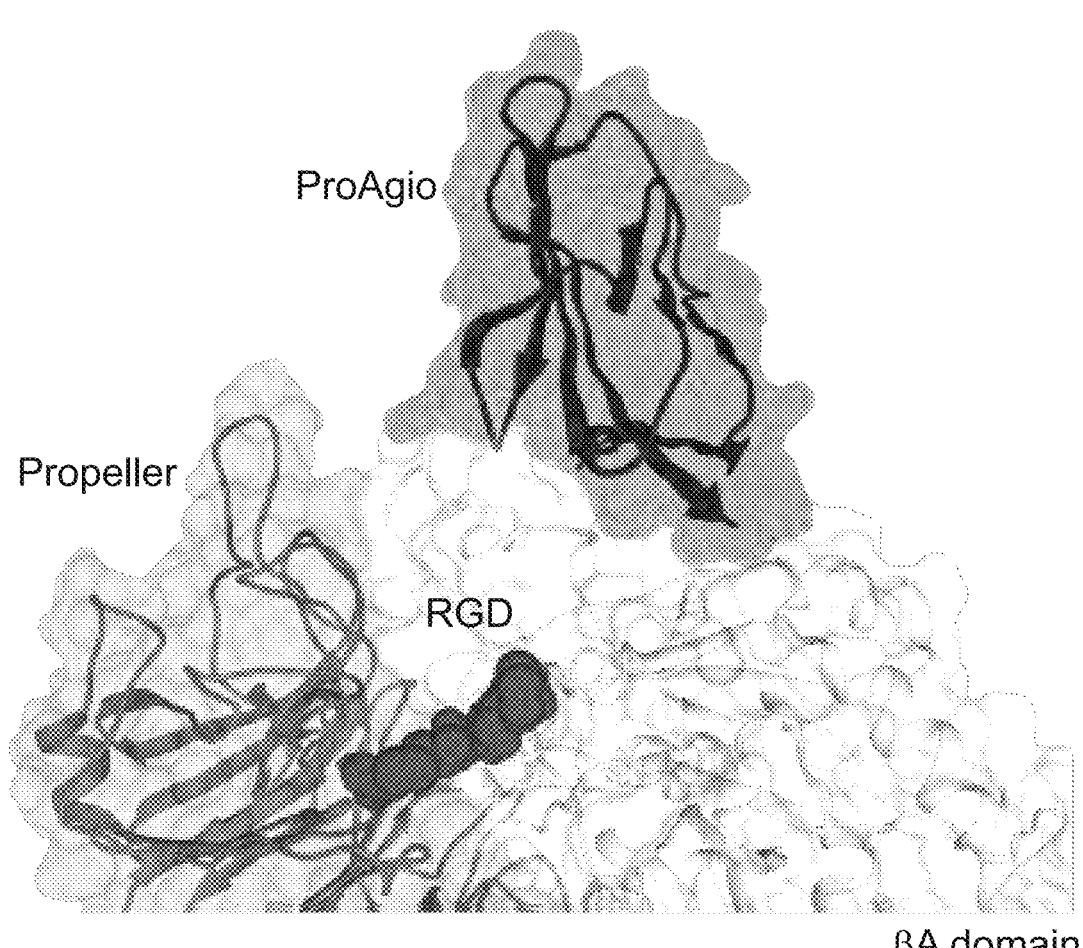
FIG. 16 illustrates mutations on the integrin β3 reduced the attachment of the integrin mutant expression cells to ProAgio according to the present disclosure.
Figure 17:
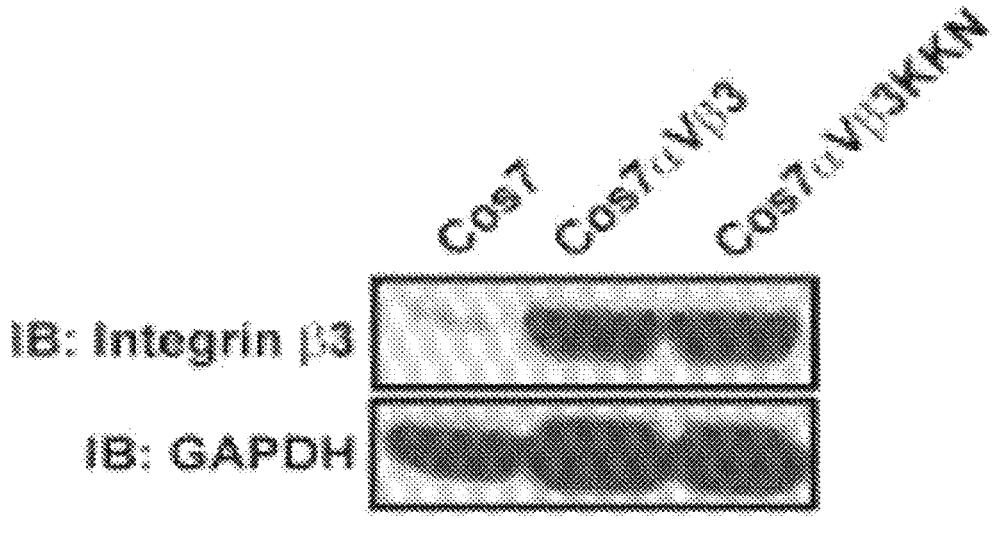
FIG. 17 illustrates mutations reduced the attachment of the mutant expressing CHO cells according to the present disclosure.
Figure 18:
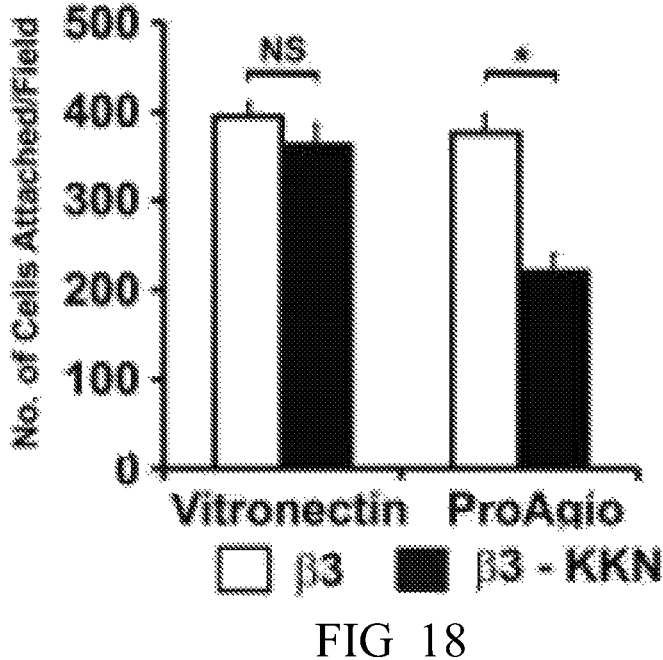
FIG. 18 is a graphical representation illustrating mutations reduced the attachment of the mutant expressing CHO cells to ProAgio according to the present disclosure.
Figure 19:
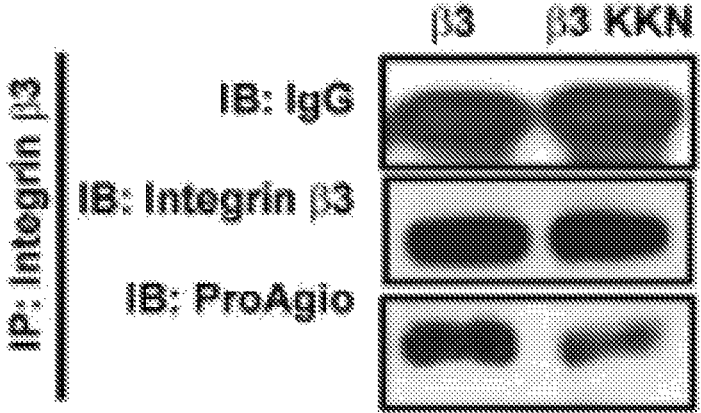
FIG. 19 illustrates mutations abolished ProAgio and integrin β3 co-immunoprecipitation according to the present disclosure.
Figure 20:
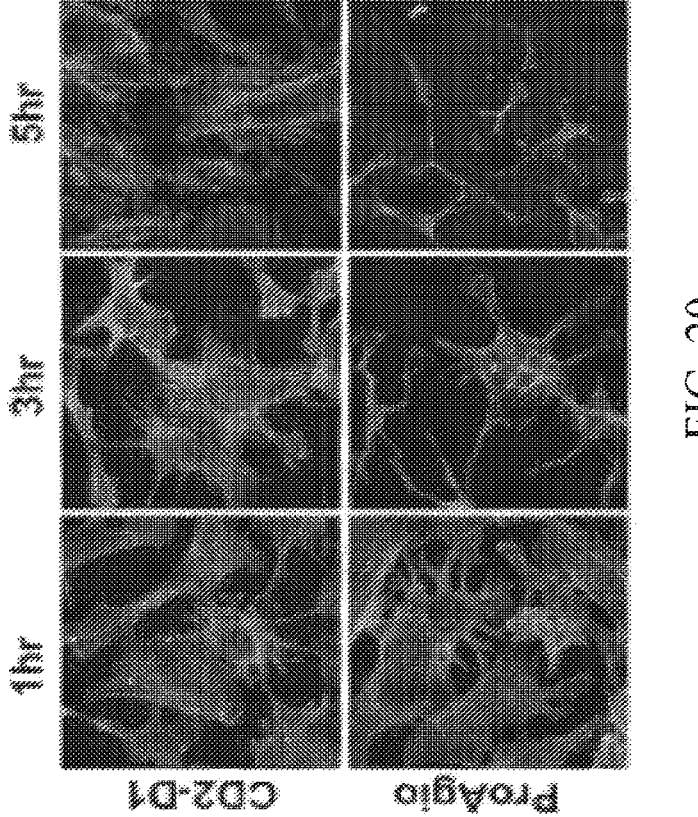
FIG. 20 illustrates actinfilament stress fibers decreased and disappeared upon the HUVEC cells being treated with ProAgio according to the present disclosure.
Figure 22:
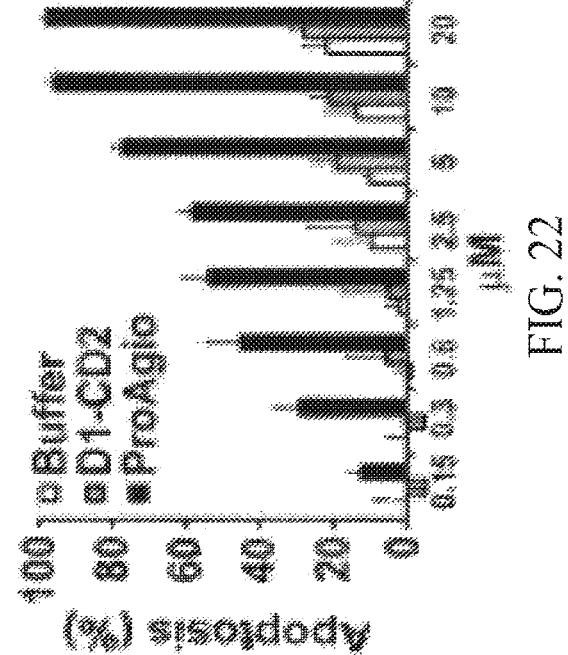
FIG. 22 is a graphical representation illustrating ProAgio induces apoptosis of HUVEC cells according to the present disclosure.

A chemical crosslink using Bis(Sulfosuccinimidyl)-glutarate (BS2G) (illustrated as FIG. 12) as a crosslinker evidences ProAgio binds to the βA groove site. This crosslinking, followed by trypsin digestion and LC-MS analyses, indicates ProAgio WEKTSDKK (SEQ ID NO:6) (aa 35-43)

crosslinked to the integrin aγ at TEMKQER (SEQ ID NO:1) (aa 116-122) (illustrated as FIGS. 13A-13C). ProAgio and integrin β3 interaction was not detected using BS2G due to steric hindrance, i.e., due to bulk volume of the crosslinking reaction group.

In response, crosslinking was re-performed using glutaraldehyde (illustrated as FIG. 14) as a crosslinker. ProAgio NLKVII (SEQ ID NO:7) (aa 99-105) crosslinked to integrin β3 FNEEVKKQ (SEQ ID NO:2) (aa 203-210) by glutaraldehyde (illustrated as FIGS. 15A-15B). This also demonstrates ProAgio interacts with integrins $\alpha_v\beta_3$ at the βA groove site.

Binding of ProAgio to the βA groove was further verified by mutational analyses. Mutations on the integrin β3 at contacts Q158A, K233A, and K234A reduced the attachment of the integrin mutant expression cells to ProAgio (illustrated as FIG. 16). Computations demonstrate the mutations weaken the ProAgio/integrins $\alpha_v\beta_3$ docking. The mutations also reduced the attachment of the mutant expressing CHO cells (illustrated as FIG. 17) to ProAgio (illustrated as FIG. 18), and abolished ProAgio and integrin β3 co-immunoprecipitation (illustrated as FIG. 19).

FIGS. 20 through 30 illustrate ProAgio's effects on cell apoptosis by promoting recruitment and activation of caspase 8 to the cytoplasmic domain of integrin β3. The formation of actin filament stress fibers and the focal adhesion complex of HUVEC cells in the presence and absence of ProAgio were analyzed to determine the effects of ProAgio treatment on integrin activity. The actin filament stress fibers decreased and disappeared upon the HUVEC cells being treated with ProAgio (illustrated in FIG. 20). Accumulation of vinculin at the tips of the stress fibers was also diminished upon treatment of the HUVEC cells with ProAgio (not illustrated). This indicates disassociation of the focal adhesion complex.

Figure 21:
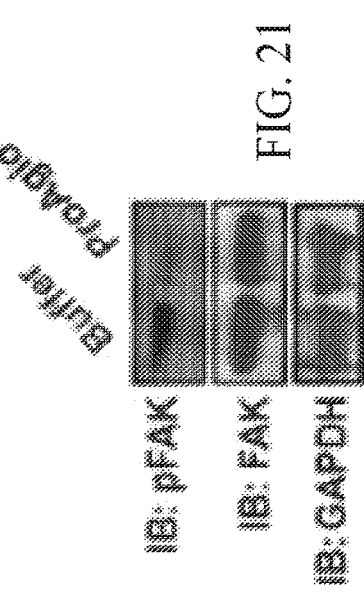
FIG. 21 illustrates ProAgio treatment leads to inactivation of FAK activated by attachment to ECM according to the present disclosure.
Figure 23:
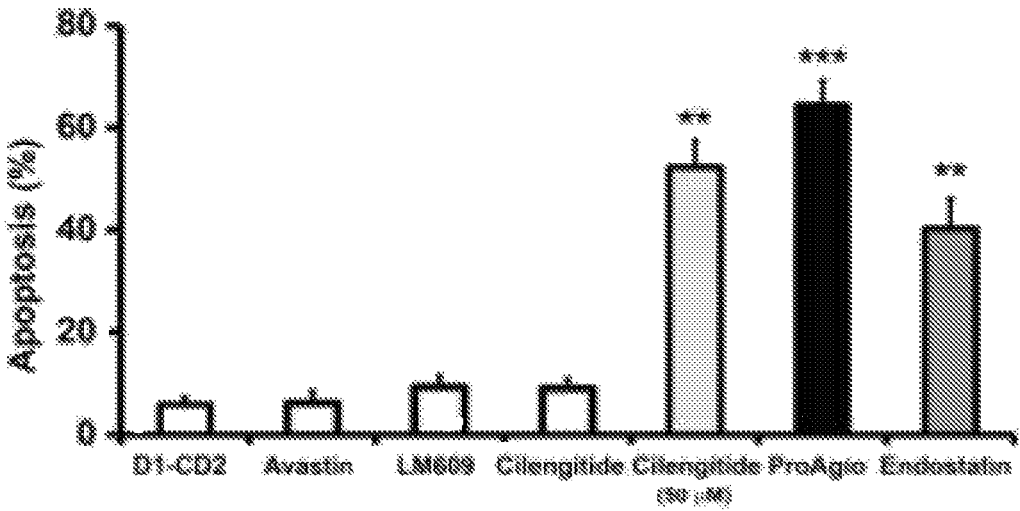
FIG. 23 is a graphical representation illustrating ProAgio is more effective in inducing apoptosis than other anti-angiogenic agents according to the present disclosure.
Figure 24:
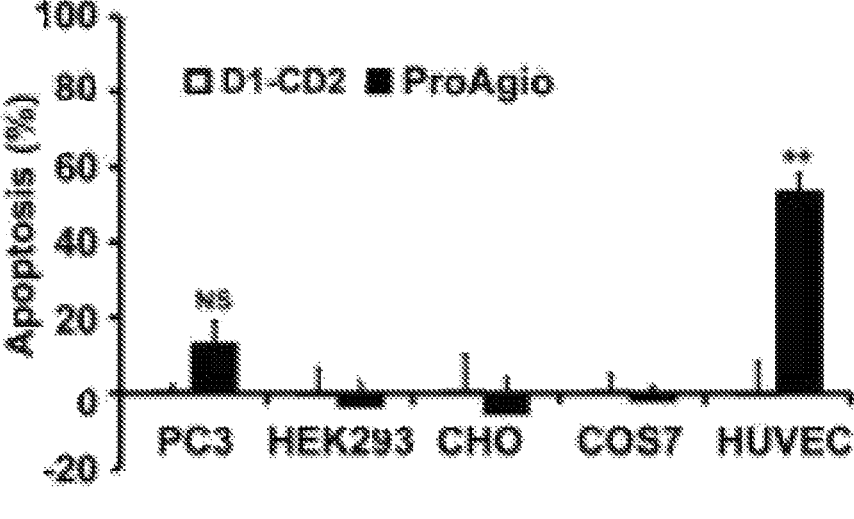
FIG. 24 is a graphical representation illustrating ProAgio induces apoptosis of HUVEC and COS-7 cells with exogenous expression of integrins according to the present disclosure.
Figure 25:
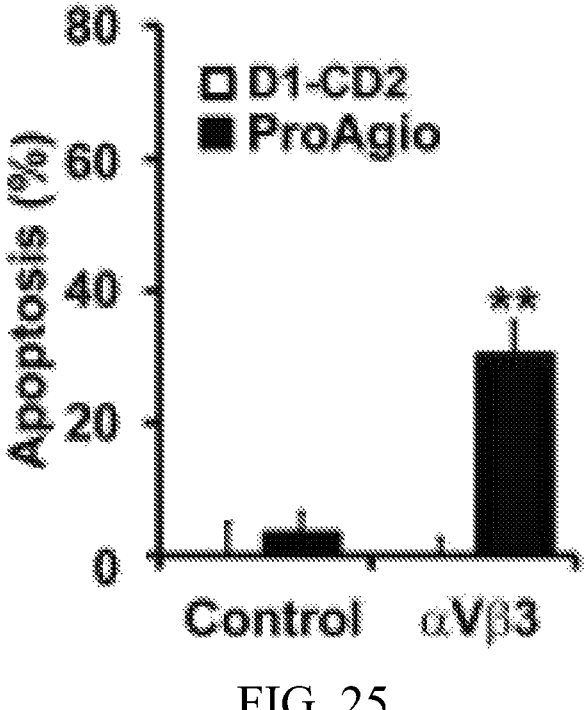
FIG. 25 is a graphical representation illustrating ProAgio induces apoptosis of HUVEC and COS-7 cells with exogenous expression of integrin according to the present disclosure.
Figure 26:
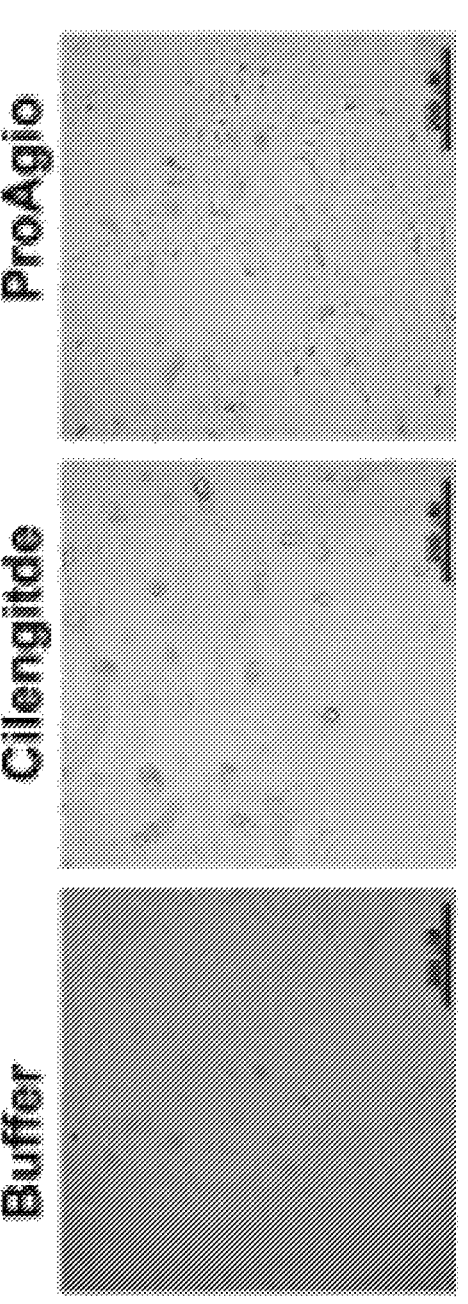
FIG. 26 illustrates ProAgio treatment does not lead to HUVEC cell floating/detaching according to the present disclosure.
Figure 27:
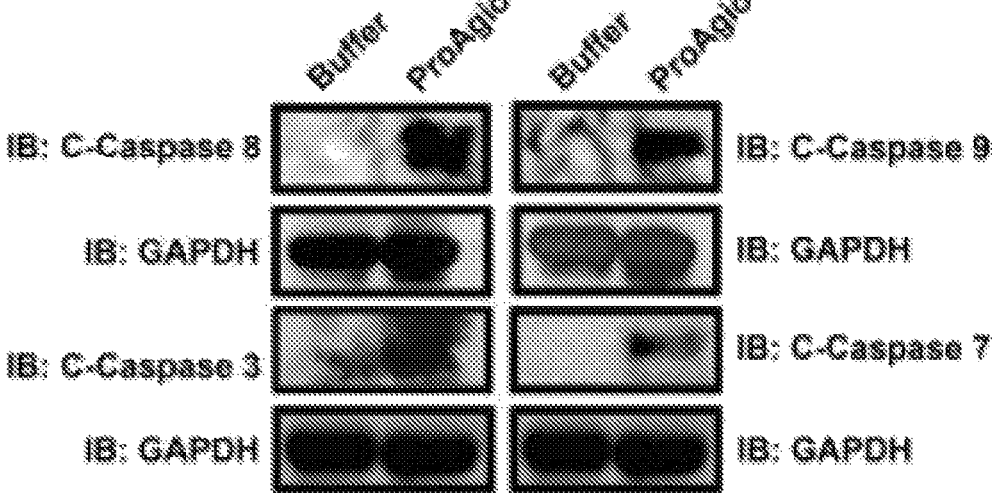
FIG. 27 illustrates the effects of ProAgio treatment on caspase 8, caspase 9, caspase 7, and caspase 3 according to the present disclosure.
Figure 28:
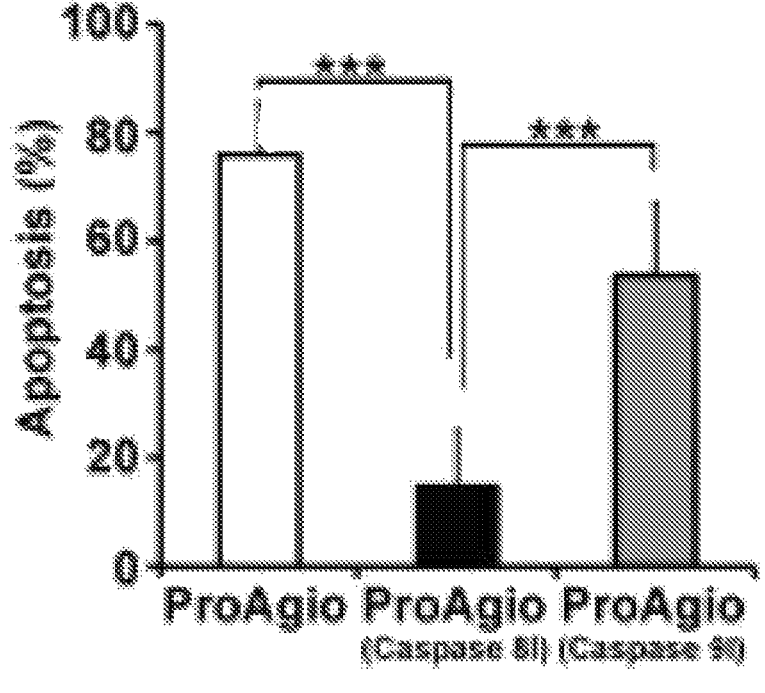
FIG. 28 is a graphical representation illustrating the effects caspase 8 inhibitor and caspase 9 inhibitor on ProAgio according to the present disclosure.
Figure 29:
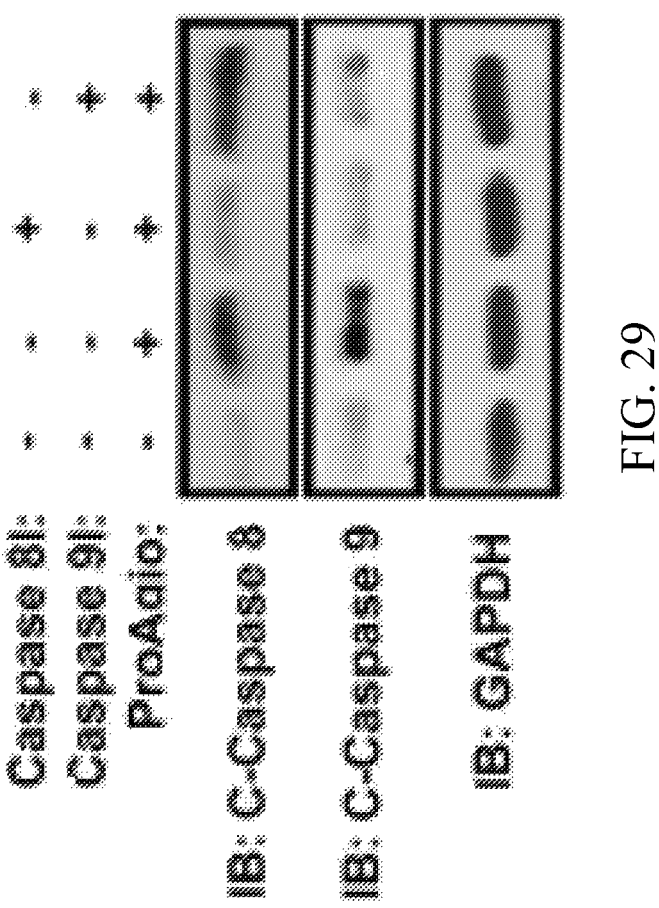
FIG. 29 illustrates the effects of caspase 8 inhibitor and caspase 9 inhibitor upon activation of each other according to the present disclosure.
Figure 30:
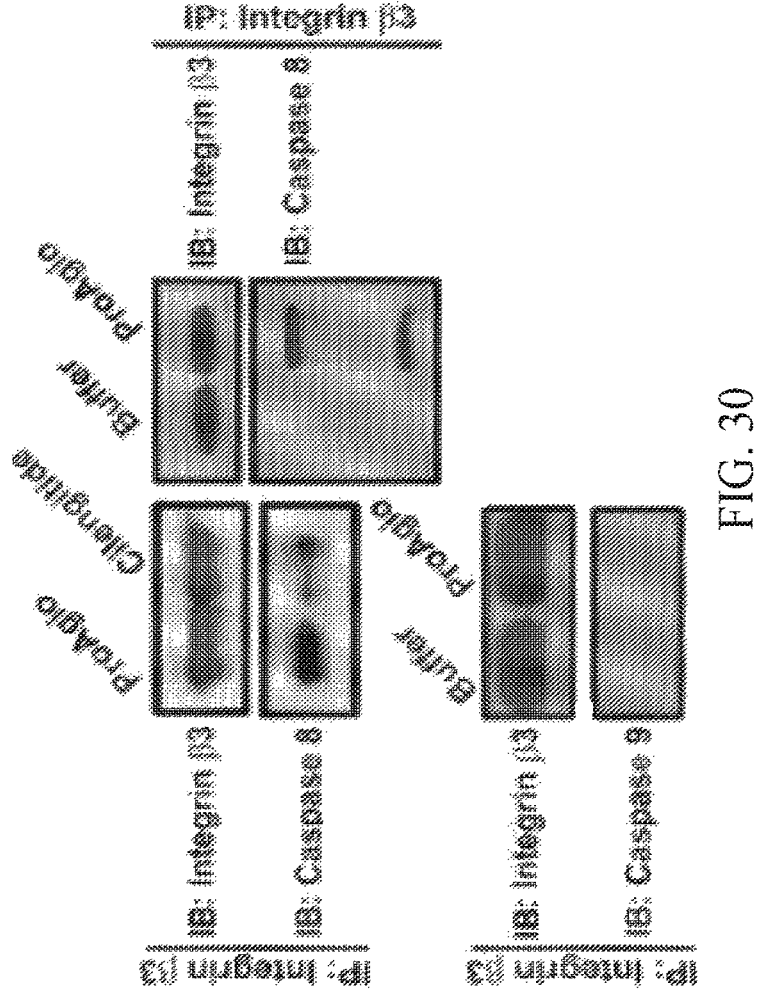
FIG. 30 illustrates the effects of Cilengitide on recruitment of caspase 8 to the integrin β3 cytoplasm domain according to the present disclosure.

Moreover, ProAgio treatment inactivates Focal Adhesion Kinase ("FAK") that was activated by attachment to ECM (illustrated in FIG. 21). Thus, ProAgio abrogates integrin functions in endothelial cells.

ProAgio also induces apoptosis of HUVEC cells. Specifically, ProAgio induces HUVEC cell apoptosis with EC50 around 1.4 uM in a 10 hour treatment (illustrated in FIG. 22).

ProAgio was additionally compared with several anti-angiogenie agents using HUVEC cells; the anti-angiogenic agents being AVASTIN, ENDOSTAR (an endostatin derivative approved for lung cancer treatment in China), LM609.® (a monoclonal antibody target at the ligand-binding site of integrin $\alpha_v\beta_3$), and Cilengitide.® (a RGD-based peptidomimetic). ProAgio was more effective in inducing apoptosis than the other anti-angiogenic agents (illustrated in FIG. 23).

Further testing was conducted to determine whether the effects of ProAgio on apoptosis induction are integrin α.sub.vβ3 dependent. Similar cell apoptosis assays were carried out with several cell lines, namely, HUVEC, PC-3, HEK, and COS-7 with or without exogenous expression of integrin $\alpha_v\beta_3$. HUVEC cells express high levels of $\alpha_v\beta_3$, PC-3 cells express marginal levels of integrin $\alpha_v\beta_3$, HEK cells express $\alpha_v$ but not $\beta_3$, and COS-7 cells do not express $\alpha_v\beta_3$. ProAgio does not induce apoptosis in the presence of PC-3, COS-7, or HEK cells. However, ProAgio induces apoptosis of HUVEC and COS-7 cells with exogenous expression of integrin αvβ3 (illustrated in FIGS. 24 and 25). Apoptosis was also observed when PC-3 cells were treated with a high concentration of ProAgio, i.e., >30 uM (not illustrated). Therefore, the effects of ProAgio in apoptosis induction is $\alpha_v\beta_3$ dependent.

To verify anti-angiogenesis activity, endothelial tube formation assay was carried out using HUVEC cells. ProAgio almost completely disrupted the endothelial tube.

In contrast to the effects of Cilengitide and other integrin targeting molecules, ProAgio treatment does not lead to HUVEC cell floating/detaching (illustrated in FIG. 26), indicating ProAgio induces apoptosis by a mechanism different from anoikis.

The activation of various caspases in HUVEC cells upon ProAgio treatment evidence the molecular mechanism by which ProAgio induces endothelial cell apoptosis. Caspase 8 and caspase 9 were strongly activated, while caspase 7 and caspase 3 were also activated (illustrated in FIG. 27).

ProAgio apoptosis induction dependence on activation of initiation caspase 8 and/or caspase 9 was also tested. Caspase 8 and caspase 9 inhibitors were utilized. The caspase 9 inhibitor did not abolish the effects of ProAgio in apoptosis induction, while the caspase 8 inhibitor largely abolished the effects of ProAgio (illustrated in FIG. 28). On the other hand, the caspase 9 inhibitor did not abrogate the activation of caspase 8, while the activation of caspase 9 was largely inhibited by the caspase 8 inhibitor (illustrated in FIG. 29), thereby suggesting the caspase 8 activation mediated the effects of ProAgio in inducing apoptosis.

Unligated integrin β3 can lead to cell apoptosis by directly recruiting caspase 8 to its cytoplasmic domain by a mechanism known as integrin mediated death ("IMD"). ProAgio may induce endothelial cell apoptosis by a mechanism similar to that of IMD, while also being different from that of other integrin antagonists. It was examined whether ProAgio treatment led to direct recruitment and activation of caspase 8 to the cytosolic site of integrin β3 by co-immunoprecipitation. Caspase 8 co-immunoprecipitated with integrin β3 upon ProAgio treatment. As a control, caspase 8 did not co-precipitate with the integrin β3 without the ProAgio treatment. Cilengitide did not recruit caspase 8 to the integrin β3 cytoplasm domain under the same conditions (illustrated in FIG. 30).

Figure 31:
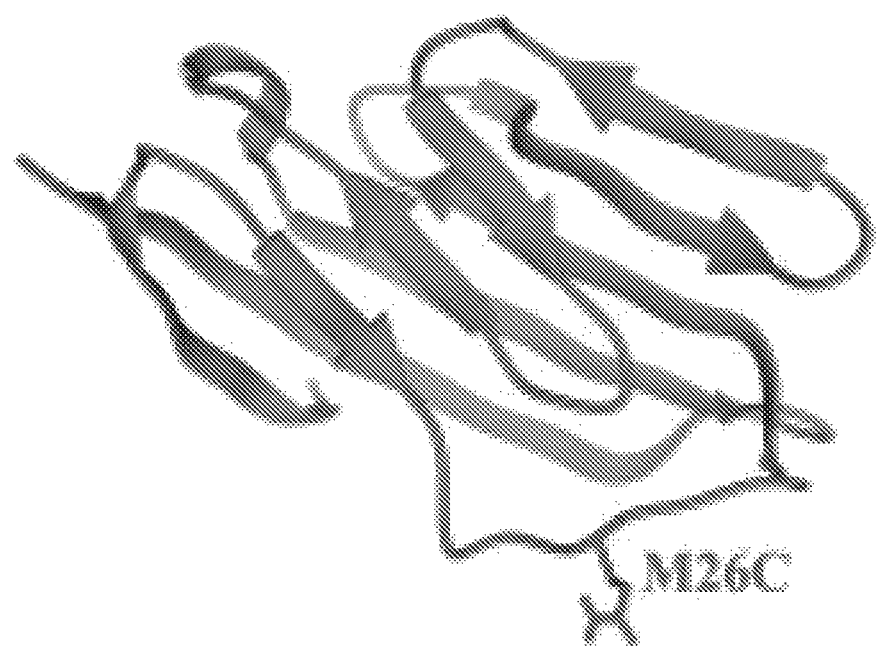
FIG. 31 illustrates PEGylation of ProAgio according to the present disclosure.
Figure 32:
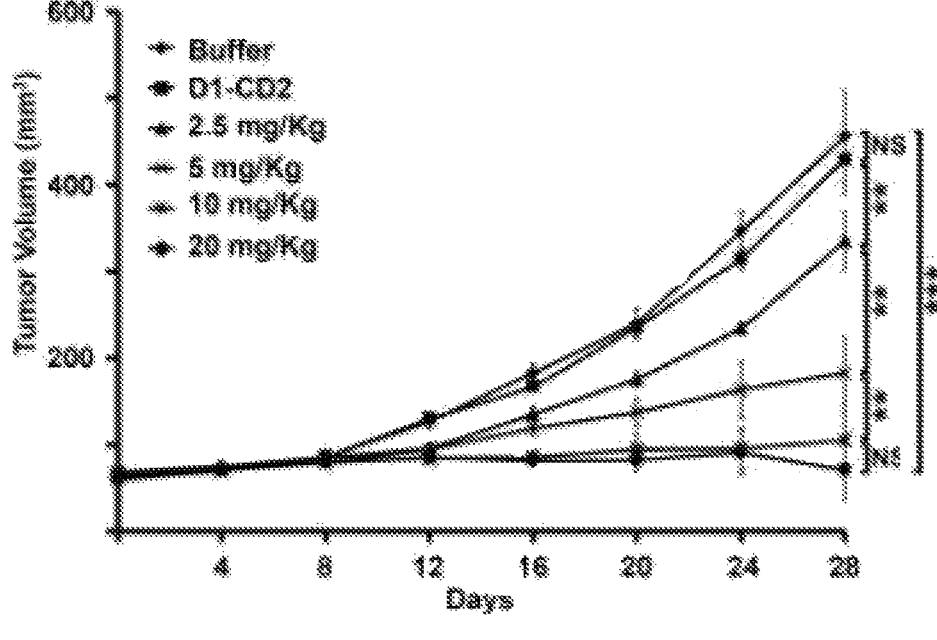
FIG. 32 is a graphical representation illustrating the effects and dosage dependency of ProAgio-PEG on tumor growth inhibition according to the present disclosure.
Figure 33:
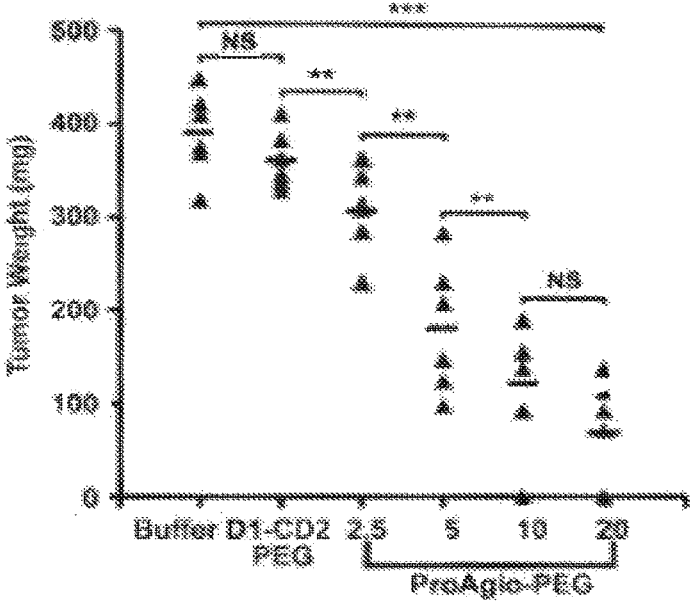
FIG. 33 is a graphical representation illustrating the effects and dosage dependency of ProAgio-PEG on tumor growth inhibition according to the present disclosure.

FIG. 31 through 43 illustrate ProAgio's effectiveness in inhibiting tumor growth and reducing tumor blood vessels. ProAgio was PEGylated with polyethylene glycol using PEG-20 kDa, a molecule with a linear-shaped PEG chain ("ProAgio-PEG"), at an introduced Cys residue (illustrated in FIG. 31). The Cys mutation was introduced at a side not involved in integrin contacting. In vitro testing with HUVEC cells indicates PEGylation of ProAgio does not result in a significant decrease in activity.

A xenograft model of PC-3 cells was generated. Tumor bearing mice were i.p. administered with various doses of ProAgio-PEG and PEGylated D1-CD2, or a buffer saline for 20 days via one dose every other day. These treatments were started at the fifth day post tumor inoculation. ProAgio-PEG inhibited tumor growth in groups receiving doses of either 10 or 20 mg/kg (with two and one tumors completely disappearing in the 20 and 10 mg/kg dose groups respectively), while tumors grew at normal rates in the mice treated with either buffer or the PEGylated D1-CD2.

The effects of ProAgio-PEG on tumor growth inhibition are dosage dependent. However, the dosage dependency is less dramatic above 10 mg/kg (illustrated in FIGS. 32 and 33).

Figure 34:
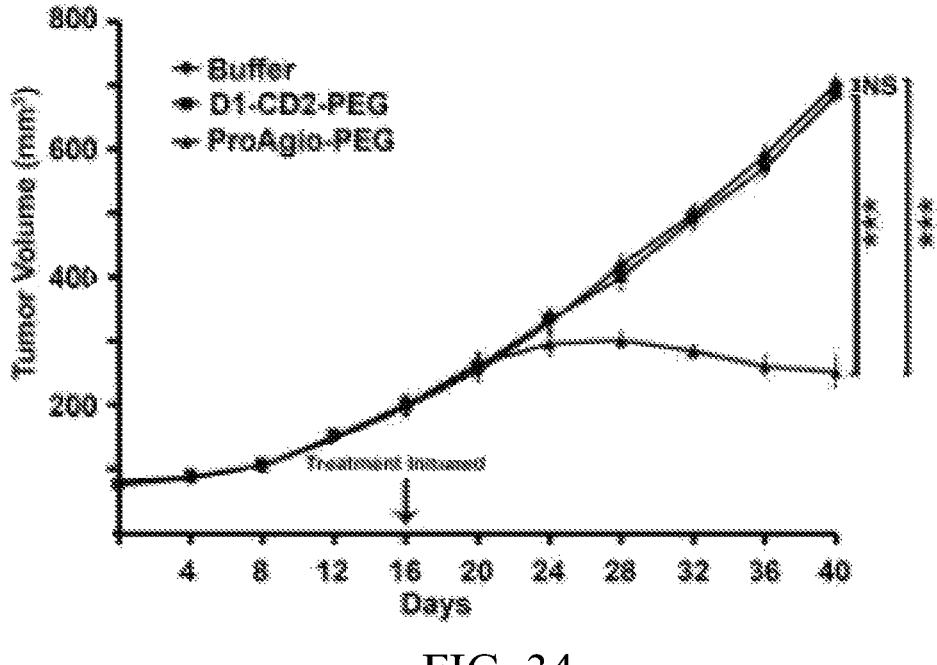
FIG. 34 is a graphical representation illustrating the effects of ProAgio-PEG when administered at a late time of tumor growth according to the present disclosure.
Figure 35:
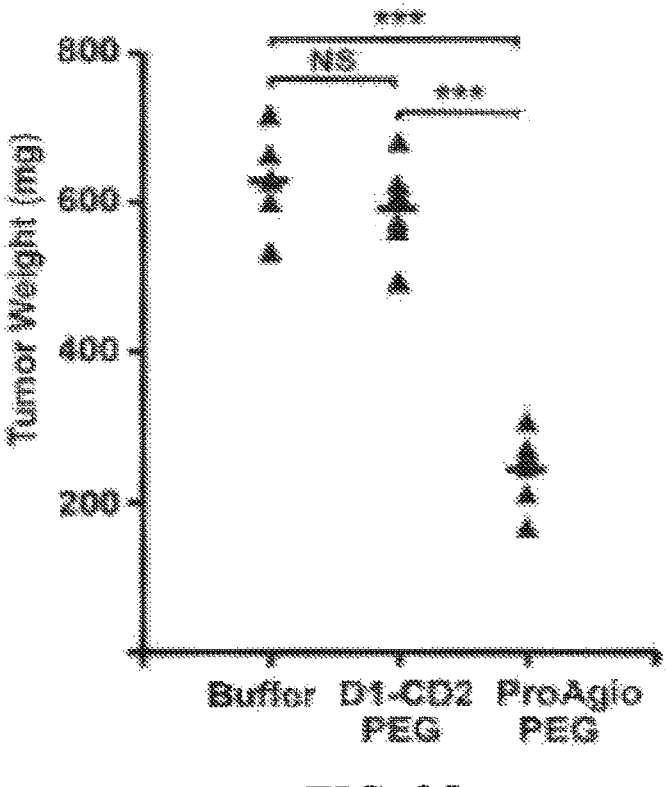
FIG. 35 is a graphical representation illustrating the effects of ProAgio-PEG when administered at a late time of tumor growth according to the present disclosure.

ProAgio-PEG is also effective when administered at a late time of tumor growth (illustrated in FIGS. 34 and 35).

Figure 36:
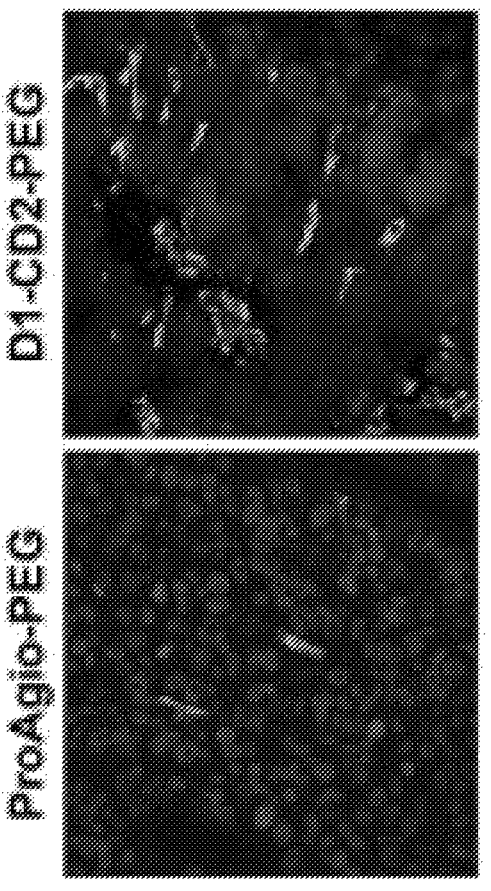
FIG. 36 illustrates immunostaining of CD31 with tissue sections prepared from collected tumors to analyze the effects of ProAgio-PEG on tumor vessels according to the present disclosure.
Figure 38:
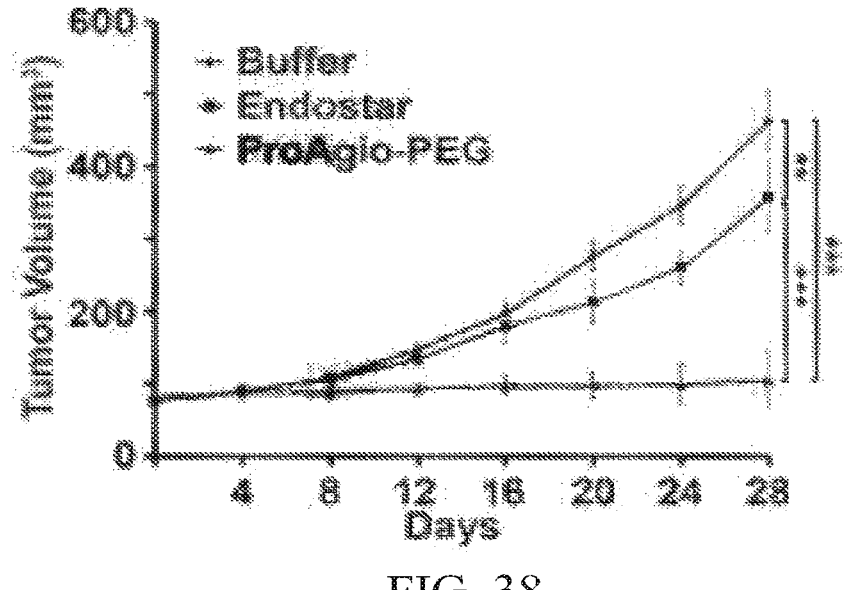
FIG. 38 is a graphical representation illustrating the effects of ProAgio-PEG as compared to AVASTIN and ENDOSTAR according to the present disclosure.
Figure 39:
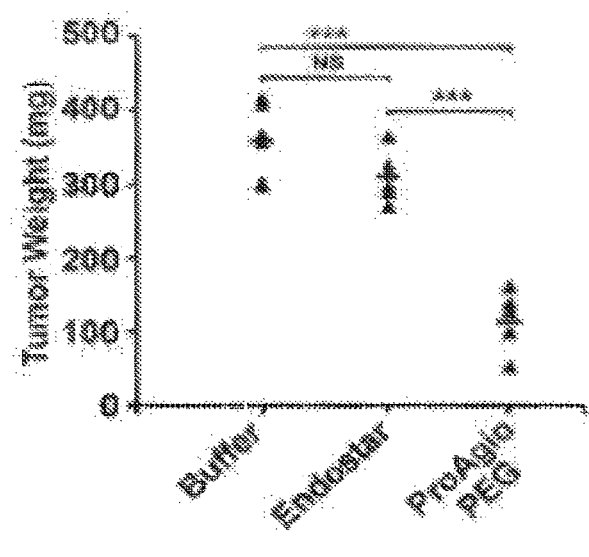
FIG. 39 is a graphical representation illustrating the effects of ProAgio-PEG as compared to AVASTIN and ENDOSTAR according to the present disclosure.
Figure 40:
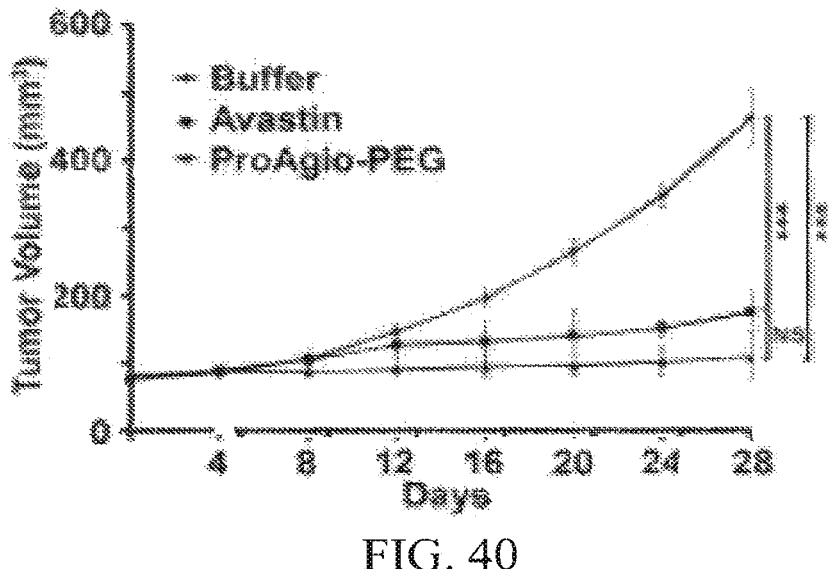
FIG. 40 is a graphical representation illustrating the effects of ProAgio-PEG as compared to AVASTIN and ENDOSTAR according to the present disclosure.
Figure 41:
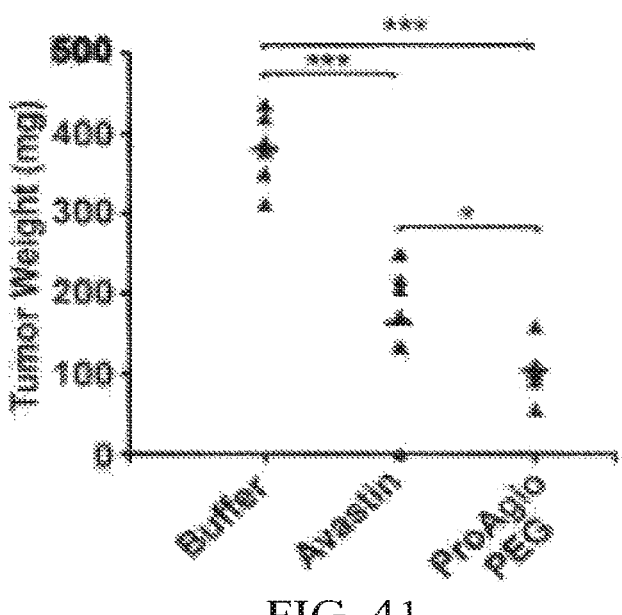
FIG. 41 is a graphical representation illustrating the effects of ProAgio-PEG as compared to AVASTIN and ENDOSTAR according to the present disclosure.
Figure 42:
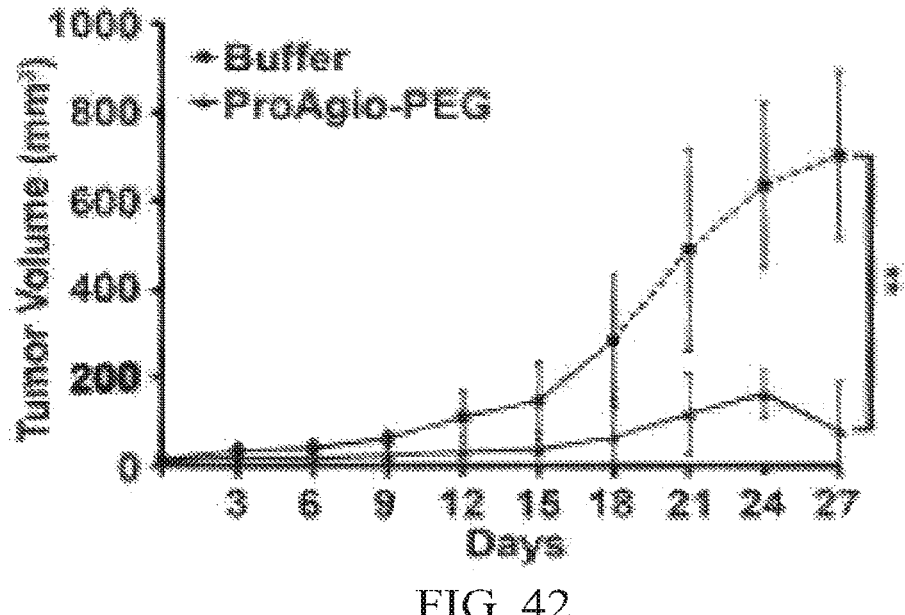
FIG. 42 is a graphical representation illustrating the effects on ProAgio-PEG on tumor growth according to the present disclosure.
Figure 43:
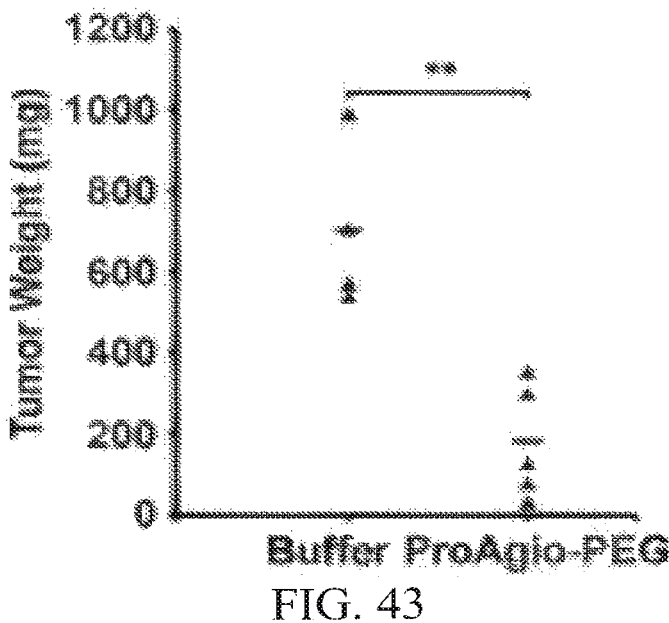
FIG. 43 is a graphical representation illustrating the effects on ProAgio-PEG on tumor growth according to the present disclosure.

Immunostaining of CD31, an endothelial marker, with tissue sections prepared from collected tumors was conducted to analyze the effects of the treatment of ProAgio- PEG on tumor vessels (illustrated in FIG. 36). ProAgio reduced the blood vessels' density, branch points, and length (illustrated in FIG. 37).

It is contemplated that that the anti-angiogenic agent may be used with Anti-cancer Supplementary Potentiating Agents, including the following Supplementary Potentiating Agents: Anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca.sup.++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor. Numerous other compounds that fall within this category of agents that are useful in combination with the anti-fi agent.

One embodiment also includes a kit for treating an angiogenic dependent condition in a mammal comprising an anti-angiogenic agent and a chemotherapeutic agent. The combination of agents is provided to allow administration in an amount and frequency therapeutically effective to produce an inhabitation or regression of angiogenesis. In certain embodiments, the anti-fibrotic agent and/or polynucleotides are administered alone or in combination with an anti-inflammatory agent. Anti-inflammatory agents that may be administered with the anti-angiogenic agents of the invention include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

Pharmaceutical agents include the following categories and specific examples. It is not intended that the category be limited by the specific examples. Those of ordinary skill in the art will be able to identify readily those pharmaceutical agents that have utility outside of the central nervous system. Numerous other compounds that fall within the categories and that are useful according to the invention.

In some embodiments, it may be desired to increase the solubility and blood circulation time of the ant-angiogenic agent. To increase polypeptide solubility, blood circulation time, polyethylene glycol may be used to derivatize polypeptides of the invention, include, for example, poly(ethylene glycol) (PEG), poly(vinylpyrrolidone), polyoxamers, polysorbate and poly(vinyl alcohol), with PEG polymers being particularly preferred. The PEG polymers are PEG polymers having a molecular weight of from about 100 to about 40,000. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions. In one example, the anti-angiogenic agent was PEGylated with a PEG-chain of 20 kDa.

The polyethylene glycol molecules (or other chemical moieties) should be attached to the polypeptide with consideration of effects on functional or antigenic domains of the polypeptide. There are a number of attachment methods available to those skilled in the art. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. One may specifically desire polypeptides chemically modified at the N-terminus. Using polyethylene glycol as an illustration of the present composition, one may select from a variety of polyethylene glycol molecules (by molecular weight, branching, etc.), the proportion of polyethylene glycol molecules to polypeptide (polypeptide) molecules in the reaction mix, the type of pegylation reaction to be performed, and the method of obtaining the selected N-terminally pegylated polypeptide. Under the appropriate reaction conditions, substantially selective derivatization of the polypeptide at the N-terminus with a carbonyl group containing polymer is achieved.

A variety of administration routes are available. The particular mode selected can depend upon the anti-angiogenic agent, the particular condition being treated and the dosage required for efficacy. These methods may be practiced using any mode of administration that is medically acceptable, meaning any mode that produces effective levels of an immune response without causing clinically unacceptable adverse effects. Certain modes of administration are parenteral routes.

Certain specific embodiments also provide pharmaceutical compositions. Such compositions comprise a therapeutically effective amount of active component (e.g., the anti-angiogenic agent, the anti-angiogenic agent plus chemotherapeutic or the anti-angiogenic agent plus anti-inflammatory agent), and a pharmaceutically acceptable carrier. Such pharmaceutical carriers can be sterile liquids, such as water and oils, including those of petroleum, animal, vegetable or synthetic origin, such as peanut oil, soybean oil, mineral oil, sesame oil and the like. Water is a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Such compositions will contain a therapeutically effective amount of the anti-angiogenic agent together with a suitable amount of carrier so as to provide the form for proper administration to the patient. The formulation should suit the mode of administration.

More specifically, the agent or pharmaceutical compositions can be tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Specific embodiments for treating and/or preventing, in whole or in part, various diseases, disorders and conditions, including, for example, methods of treating a subject having or suspected of having or predisposed to, or at risk for fibrosis, and various fibrotic diseases, disorders, or conditions characterized in whole or in part by (1) fibrous material, (2) excess production of fibrous material within the extracellular matrix, and/or (3) replacement of normal tissue elements by abnormal, non-functional, and/or excessive accumulation of matrix-associated components, comprising administering a composition comprising the polypeptide specifically binds to integrin α.sub.vβ3 at the α2 helix, B—C' loop and α2-α3' loop.

It is contemplated that the anti-angiogenic agent can be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter.

In a specific embodiment, it may be desirable to administer the anti-angiogenic agent locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. When administering a polypeptide, care should be taken to use materials to which the polypeptide does not absorb.

In a specific embodiment where the anti-angiogenic agent is a nucleic acid encoding a polypeptide, the nucleic acid can be administered in vivo to promote expression of its encoded polypeptide, by constructing it as part of an appropriate nucleic acid expression vector and administering it so that it becomes intracellular, e.g., by use of a retroviral vector, or by direct injection, or by use of microparticle bombardment, or coating with lipids or cell-surface receptors or transfecting agents, or by administering it in linkage to a homeobox-like peptide which is known to enter the nucleus, etc. Alternatively, a nucleic acid can be introduced intracellularly and incorporated within host cell DNA for expression, by homologous recombination.

Other embodiments are directed to vectors containing a polynucleotide encoding anti-angiogenic agent, host cells, and the production of anti-angiogenic agent by synthetic and recombinant techniques. The vector may be, for example, a phage, plasmid, viral, or retroviral vector. Retroviral vectors may be replication competent or replication defective. In the latter case, viral propagation generally will occur only in complementing host cells. The polynucleotides encoding the anti-angiogenic agent may be joined to a vector containing a selectable marker for propagation in a host. Generally, a plasmid vector is introduced in a precipitate, such as a calcium phosphate precipitate, or in a complex with a charged lipid. The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated. As indicated, the expression vectors will preferably include at least one selectable marker.

It is contemplated that regulatory genes and sequence may use with the expression and replication of the anti-angiogenic agent. The nature of the regulatory sequences for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Promoters may be constitutive or inducible. Regulatory sequences may also include enhancer sequences or upstream activator sequences, as desired.

In one embodiment, polynucleotides encoding the anti-angiogenic agent may be fused to polynucleotides encoding signal sequences which will direct the localization of a polypeptide to particular compartments of a prokaryotic or eukaryotic cell and/or direct the secretion of a polypeptide. For example, in E. coli, one may wish to direct the expression of the protein to the periplasmic space. Several vectors are commercially available for the construction of fusion proteins which will direct the localization of a protein.

One specific embodiment provides stents, comprising a generally tubular structure (which includes for example, spiral shapes), the surface of which is coated with an anti-angiogenic agent as described above. A stent can be a scaffolding, usually cylindrical in shape, that may be inserted into a body passageway (e.g., bile ducts) or a portion of a body passageway, which has been narrowed, irregularly contoured, obstructed, or occluded by a disease process (e.g., ingrowth by a tumor) in order to prevent closure or reclosure of the passageway.

One specific embodiment also provides use of an anti-angiogenic agent a wide variety of surgical procedures. For example, within one aspect of the present invention an anti-angiogenic protein (in the form of, for example, a spray or film) may be utilized to coat or spray an area prior to removal of a tumor, in order to isolate normal surrounding tissues from malignant tissue, and/or to prevent the spread of disease to surrounding tissues. Within yet other aspects of the present invention, surgical meshes which have been coated with anti-angiogenic protein may be utilized in any procedure wherein a surgical mesh might be utilized.

The examples which follow are set forth to aid in understanding the invention, but are not intended to, and should not be construed as, limiting the scope of the invention in any manner.

Examples

Experiments were conducted to compare the effect of ProAgio-PEG v. AVASTIN and ProAgio-PEG v. ENDO-STAR using PC-3 xenografts. ProAgio-PEG was more effective in inhibiting tumor growth as compared to AVASTIN and ENDOSTAR (illustrated in FIGS. 38-41).

Moreover, ProAgio-PEG treatment leads to a higher degree of vessel reduction than those of AVASTIN and ENDOSTAR (not illustrated).

Tumor angiogenesis is generally affected by the microenvironment surrounding the tumor. Accordingly, an orthotopic model with immune-compatible mice was conducted. Specifically, experiments were conducted with murine breast 4T–1 cells using Balb/c mice. The tumor bearing mice were treated by the same dose schedule of either ProAgio-PEG or D1-CD2-PEG. Treatment was started on the fifth day post tumor inoculation. There is a significant difference in tumor growth between the ProAgio-PEG treated group and the buffer treated group (illustrated in FIGS. 42 and 43), indicating ProAgio is effective in inhibiting tumor growth with orthotopic models.

Figure 44:
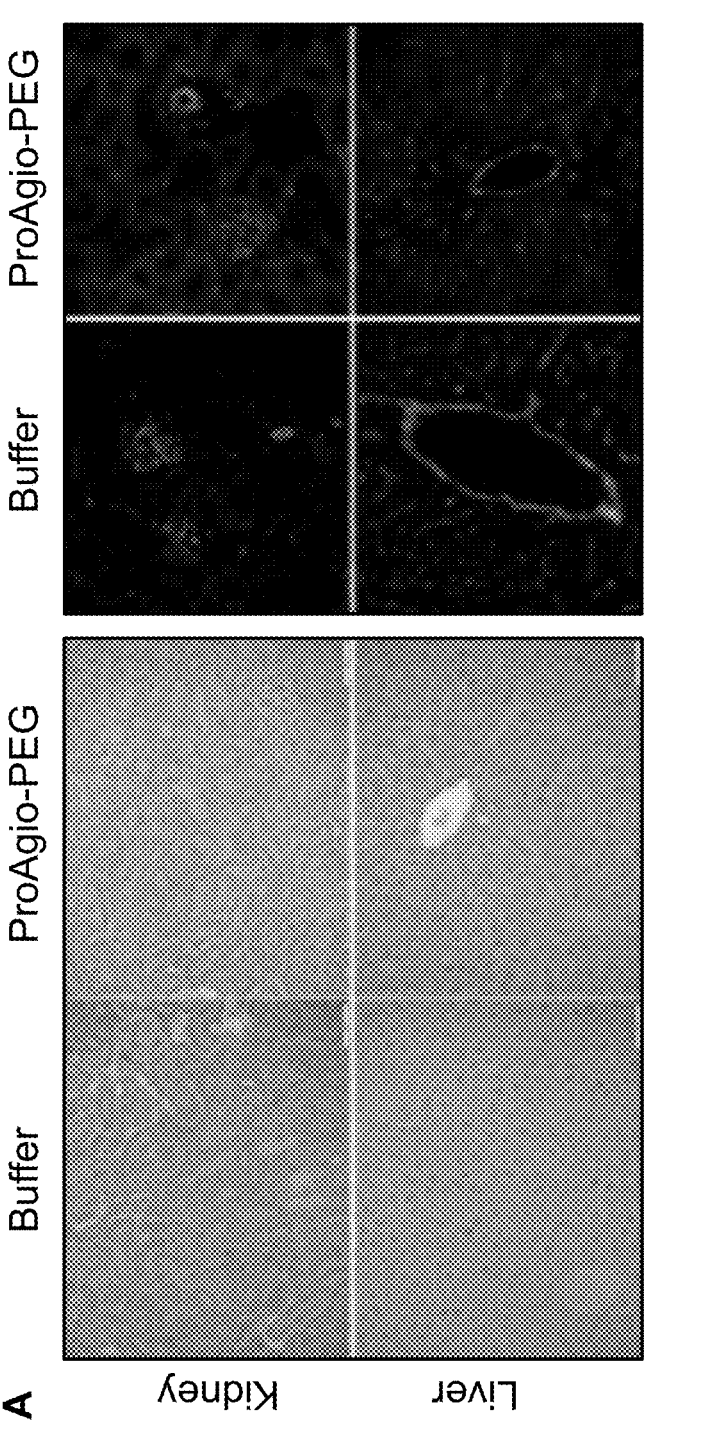
FIG. 44 illustrates the effects of ProAgio-PEG on tissue according to the present disclosure.
Figure 45:
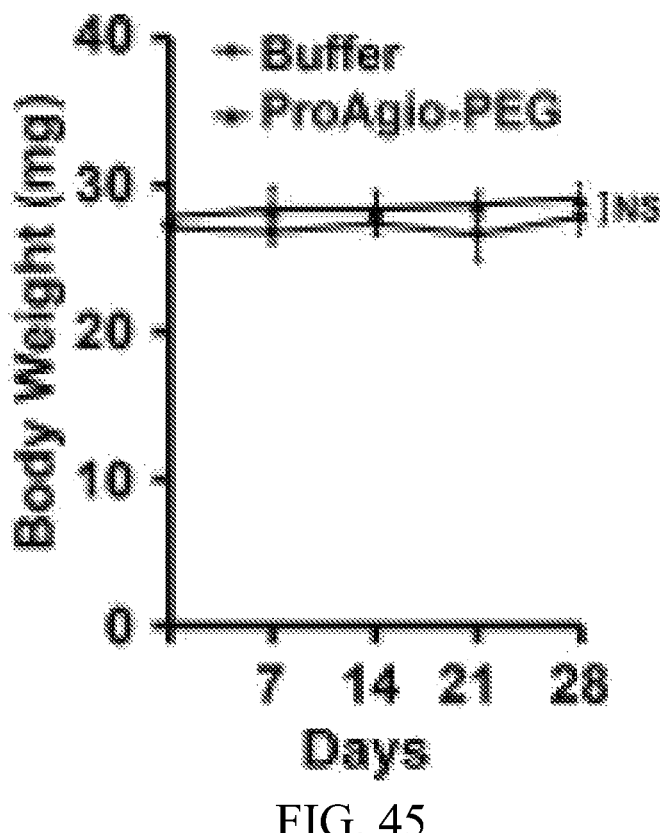
FIG. 45 is a graphical representation illustrating the effects of ProAgio-PEG on weight gain or loss according to the present disclosure.

FIGS. 44 and 45 demonstrate the non-toxicity of ProAgio to normal tissue and organs. A good anti-angiogenesis agent should be minimally toxic to existing blood vessels in normal tissue/organs. To assess this attribute of ProAgio, tissue sections from liver, lung, heart, and kidney of mice treated by different agents were prepared. The tissue sections were analyzed by Hematoxylin and Eosin ("H & E") staining and immunostaining. H & E staining revealed ProAgio does not cause obvious abnormality in tissue anatomy structure or damage, e.g., lesion/necrosis (illustrated in FIG. 44). Immunofluorescence staining using an anti-CD31 antibody indicates ProAgio-PEG disrupts or reduces blood vessels in the liver, lung, heart, or kidney less than PEGy-lated D1-CD2 or buffer saline (illustrated in FIG. 44). Further, ProAgio does not cause abnormal weight gain or loss (illustrated in FIG. 45).

To further analyze toxicity of ProAgio, healthy CD-I mice were i.v. administered three doses of 60 mg/kg of ProAgio-PEG over 48 hours. The mice were observed for 14 days. All the mice behaved normally. Blood and urine samples were collected. Plasma AST/ALT, TnT, creatinine, and urine albumin were examined 48 hours after administration of the agents. The examination indicated ProAgio-PEG at these doses does not cause damage to the mice's liver, kidney, or heart (not illustrated).

Figure 46:
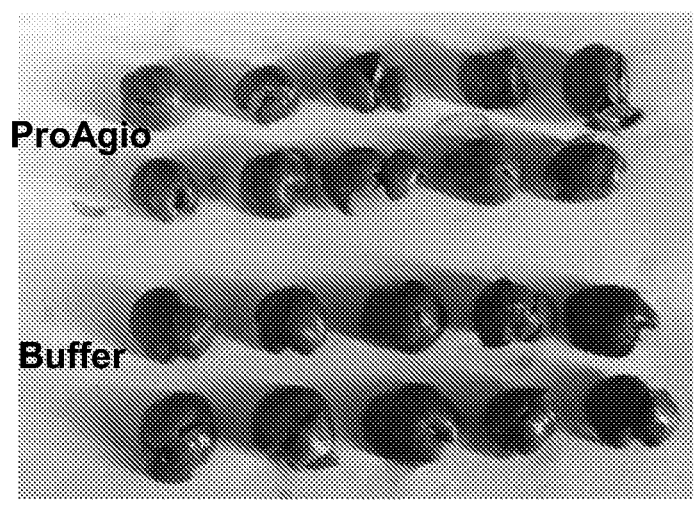
FIG. 46 illustrates the effects of ProAgio on livers from fibrosis mice according to the present disclosure.
Figures 47, 48:
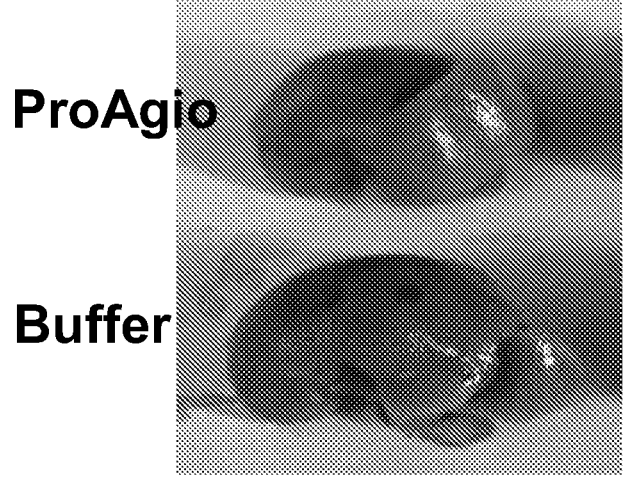
FIG. 47 illustrates the effects of ProAgio on livers from fibrosis mice according to the present disclosure.
FIG. 48 is a tabular representation illustrating the effects of ProAgio on livers from fibrosis mice according to the present disclosure.

FIGS. 46-50 illustrate the treatment of fibrosis diseases and other diseases utilizing ProAgio. Specifically, FIGS. 46-48 illustrate the effects of ProAgio on liver fibrosis mice (Balb/c mice). Liver fibrosis was induced over a six week span using two doses of 250 mg/kg a week plus 10% alcohol in the mice's drinking water. Immediately following fibrosis inducement, ProAgio (10 mg/kg) or buffer was i.p. administered to the mice ten times. The first four doses were administered daily, and the subsequent six doses were administered once every other day. FIG. 46 depicts treated livers from fibrosis mice. FIG. 47 depicts enlarged views of the treated livers from fibrosis mice. FIG. 48 evidences the liver weight of the alcohol and buffer or alcohol and ProAgio treated mice. SD is the standard deviation and the 13 value was calculated using an unpaired two-tailed t-test. Of importance, the liver sizes and weights from the ProAgio treatment group were smaller and lighter (approximately 35%-45% on average) than those in the buffer treatment group.

FIG. 49 illustrates TIMP1 levels (ng/g liver sample) in liver extracts prepared from livers collected from mice treated with alcohol and buffer or alcohol and ProAgio. The TIMP1 levels in liver extracts of the ProAgio treated group was about 5 times less than that in the buffer treated group. Further, MMP2 levels in the liver extracts of the ProAgio treated group was about 30% more than that of the buffer treated group (not illustrated). SD is the standard deviation and the $\beta$ value was calculated using an unpaired two-tailed t-test.

In an unillustrated experiment, liver fibrosis was induced by administering 250 mg/kg of 10% alcohol feeding treatment twice a week for eleven weeks. 10 mg/kg of either ProAgio or buffer saline was subsequently i.p. administered. The first three doses were administered daily and the subsequent seven doses were administered once every other day, starting at twelve weeks from the first feeding treatment. Four mice died in the buffer treated group and no mice died in the ProAgio treated group. The liver sizes and weights from the ProAgio treatment group were smaller and lighter (.apprxeq.50%-60% on average) than that of the buffer treatment group.

In another unillustrated experiment, TIMP1 and MMP2 measurements were determined. TIMP1 levels in liver extracts of the ProAgio treated group was about 7 times less than that in the buffer treated group. Moreover, MMP2 levels in liver extracts of the ProAgio treated group was about 25% more than that of the buffer treated group.

Figure 50:
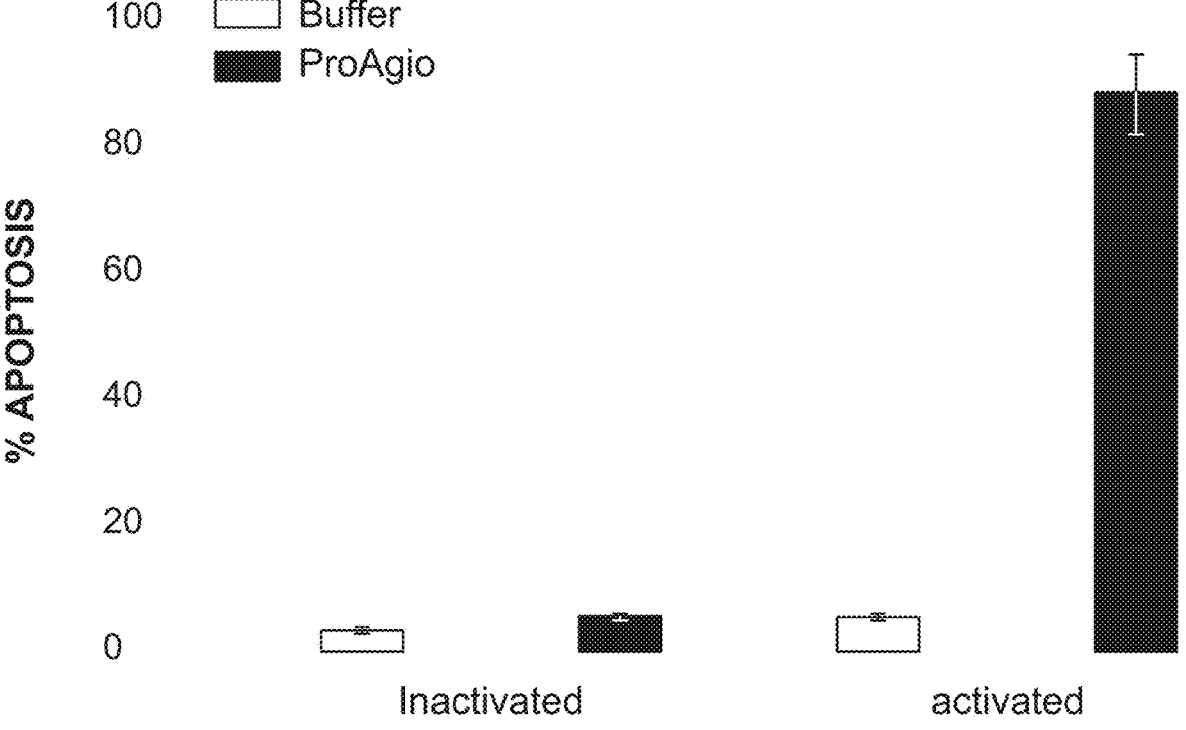
FIG. 50 is a graphical representation illustrating the effects of ProAgio on apoptosis of primary human hepatic stellate cells according to the present disclosure.

A cell experiment was also performed. A main cause for liver fibrosis is activation of hepatic stellate cells. FIG. 50 illustrates the effects of ProAgio on apoptosis of primary human hepatic stellate cells ("hHSCs"). The hHSCs were activated by culture in uncoated plastic culture plates for 8 days. The inactivated hHSCs were the cells in the first day of culture. The inactivated or activated hHSCs were treated with 5 μm ProAgio (filled bars) or buffer (open bars). Apoptosis was measured by an apoptosis kit and presented as % apoptosis by defining inactivated cells without any treatment as 0%. Treatment of activated and inactivated hHSCs with ProAgio showed that ProAgio effectively leads to apoptosis of activated hHSCs, while ProAgio had no effects on inactivated hHSCs. The error bars depict standard deviations across five independent experiments.

Figure 51:
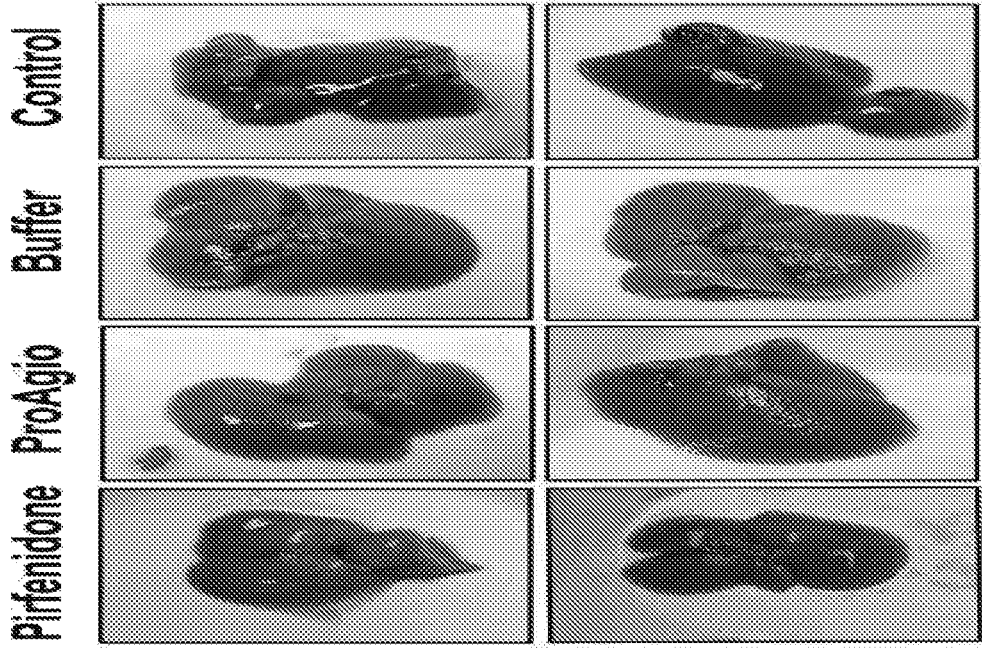
FIG. 51 illustrates the effects of ProAgio on livers from fibrosis mice according to the present disclosure.
Figure 52:
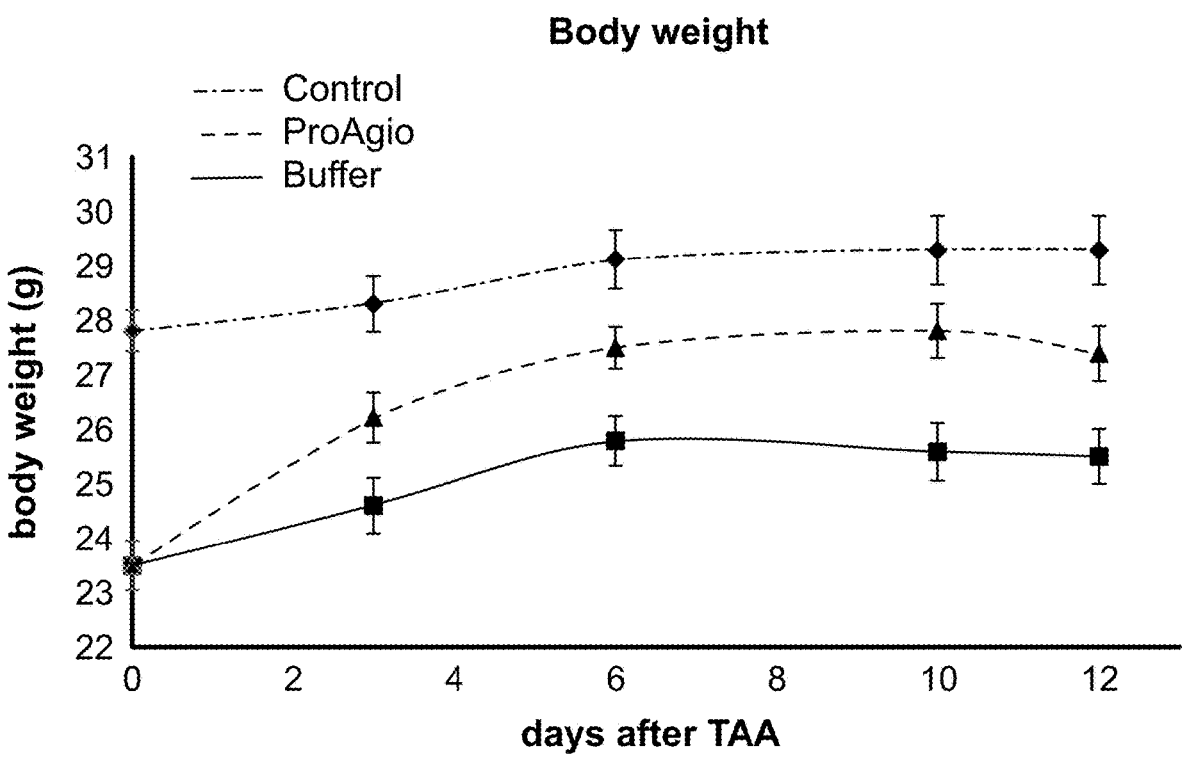
FIG. 52 is a graphical representation illustrating the effects of ProAgio on mice body weight according to the present disclosure.
Figure 53:
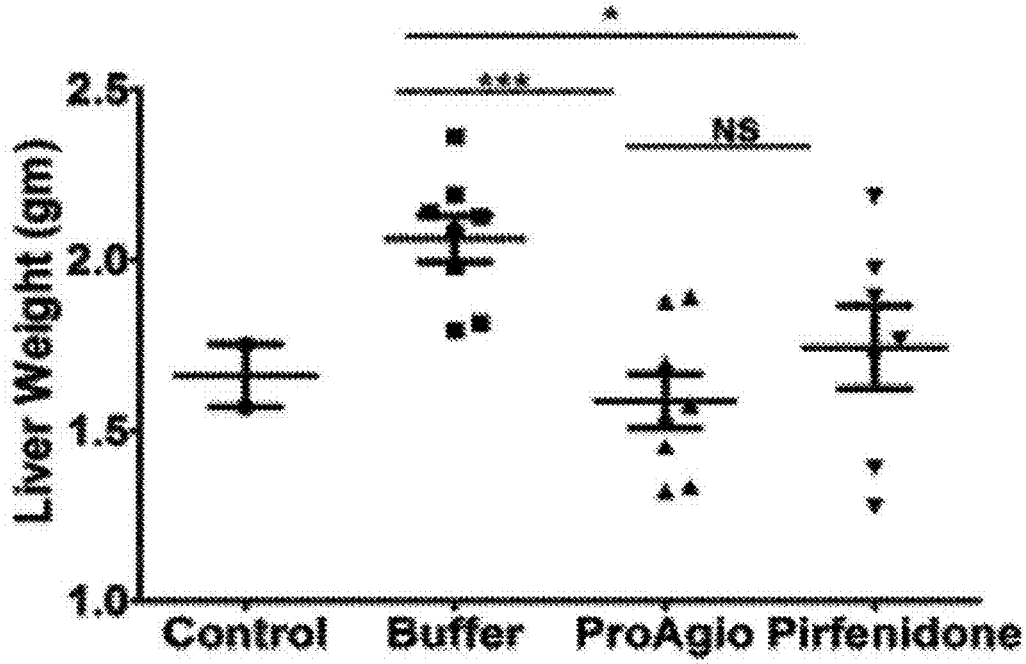
FIG. 53 is a graphical representation illustrating the effects of ProAgio on livers of fibrosis mice according to the present disclosure.

FIGS. 51-53 illustrate an experiment demonstrating the effects of ProAgio on liver fibrosis mice. Liver fibrosis was induced using 250 mg/kg of TAA+10% alcohol feeding treatment administered twice a week for twelve weeks. Treatments were subsequently i.p. administered. The first three treatment doses were administered daily and the subsequent 6 treatment doses were administered once every other day. The three treatment groups included 10 mg/kg of ProAgio (8 mice per group), 20 mg/kg of ESBRIET (a newly approved drug for lung fibrosis treatment) (8 mice per group), and buffer saline (8 mice per group). One mouse in the buffer group and once mouse in the ESBRIET group died.

Figure 54A:
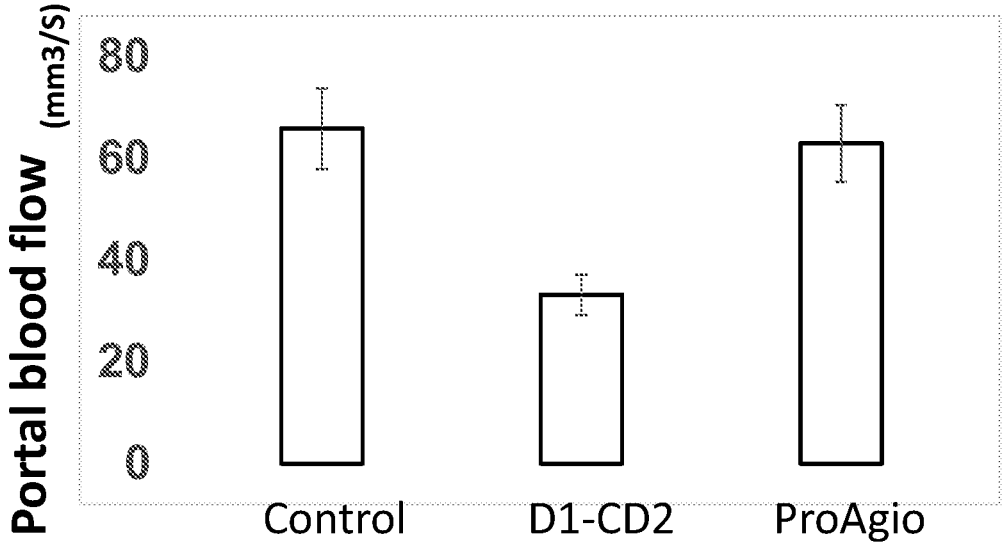
FIGS. 54A and 54B is a graphical representation illustrating the effects of ProAgio concentration on liver fibrosis.
Figure 54B:
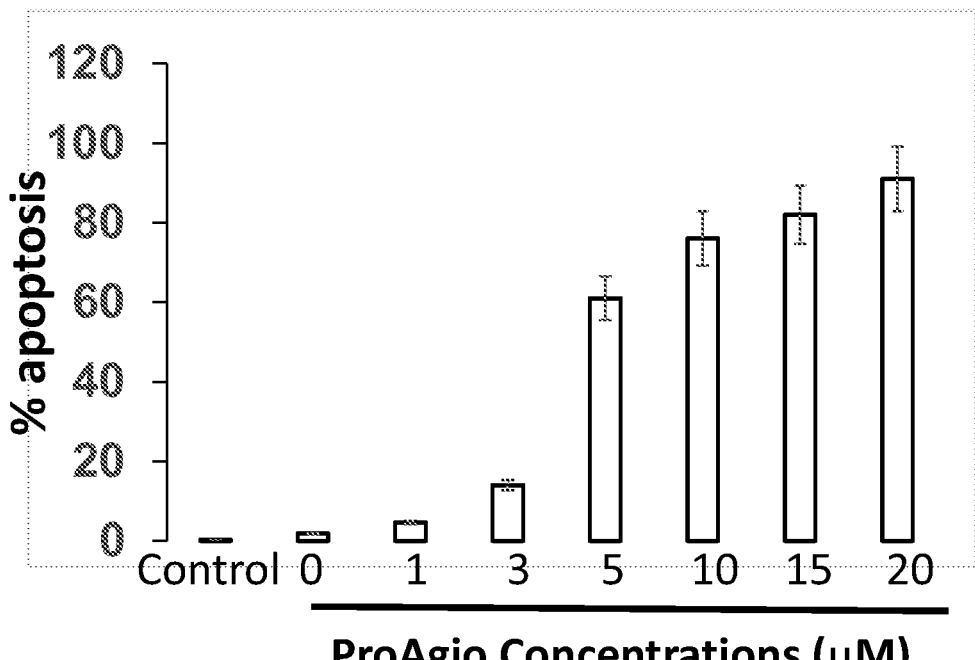

FIGS. 54A through 54B shows the effect of ProAgio on fibrotic livers. Stellate cells are believed to be a major source of extracellular matrix in the liver. Actual FIG. 54A Effects of blood flow in fibrotic liver upon ProAgio treatment. Liver fibrotic mice were treated by indicated agents. The blood flow through portal vein was measured by Doppler imaging, and presented as mm3 per second. Control is the measurement of mice without induction of fibrosis. Error bars are standard deviations of measurement of six mice. FIG. 54B shows apoptosis of activated liver sinusoidal endothelial cells (LSEC) was induced by ProAgio. Human primary LSEC were activated in culture without VEGF. The activated LSEC were treated by ProAgio at indicated concentration for 10 hours. Control is the LSEC without activation. Apoptosis is presented as % apoptosis. Error bars are standard deviations of five independent experiments. ProAgio not only reduced fibrosis but also normalized the liver vessels.

Figure 55A:
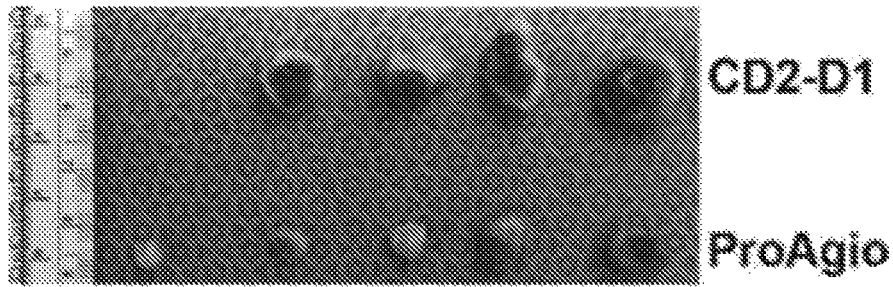
FIG. 55A though 55D show the results of ProAgio as treatment of breast cancer.
Figure 55B:
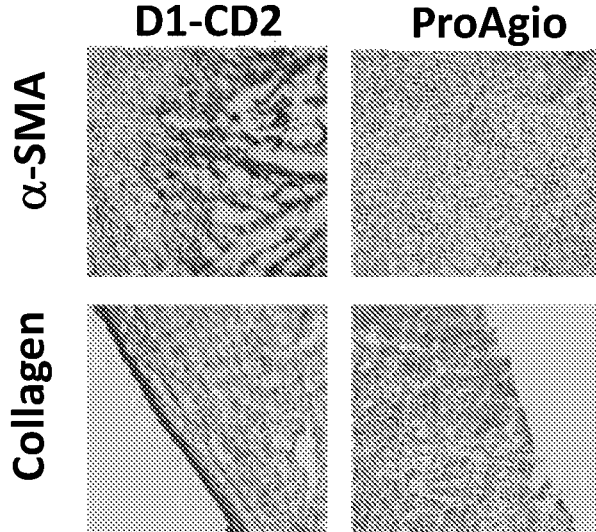
Figure 55C:
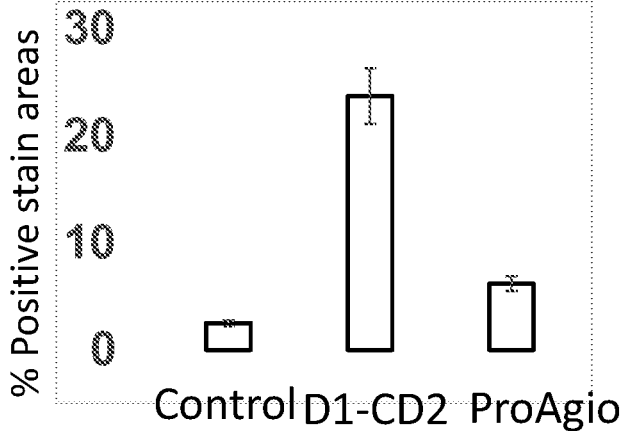
Figure 55D:
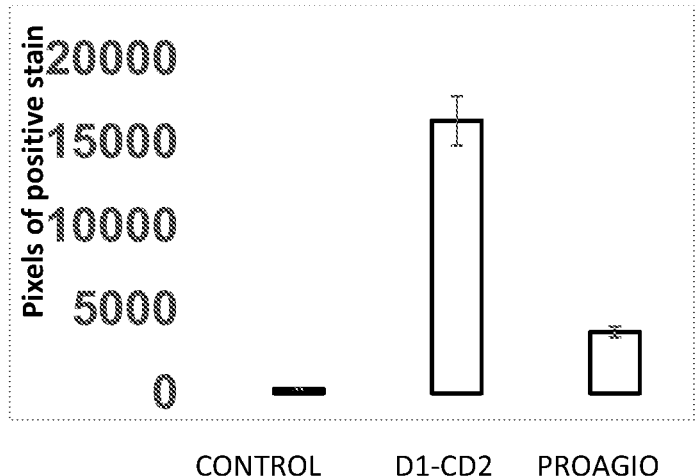

FIG. 55A though 55D show the results of ProAgio as treatment of breast cancer. Murine breast cancer 4T–1 (a well-known breast cancer model) were treated by ProAgio 10 mg/kg for 10 doses. FIG. 55A shows that the tumor size at end point (One tumor is omitted due to oversize and pre-termination of experiment by IACUC regulation). FIG. 55B shows representative images of sirius red (Collagen) and α-SMA indicating the levels of myofibroblast stains of tissue sections from the tumors. FIG. 55C shows a quantitation of sirius red stain or stain, which is presented as percentage of stained areas in each view field. FIG. 55D shows another quantitation of α-SMA, which is presented as pixels of positive stains in each view field. Error bars in (C) and (D) are standard deviations of measurement from five mice.

Figure 56:
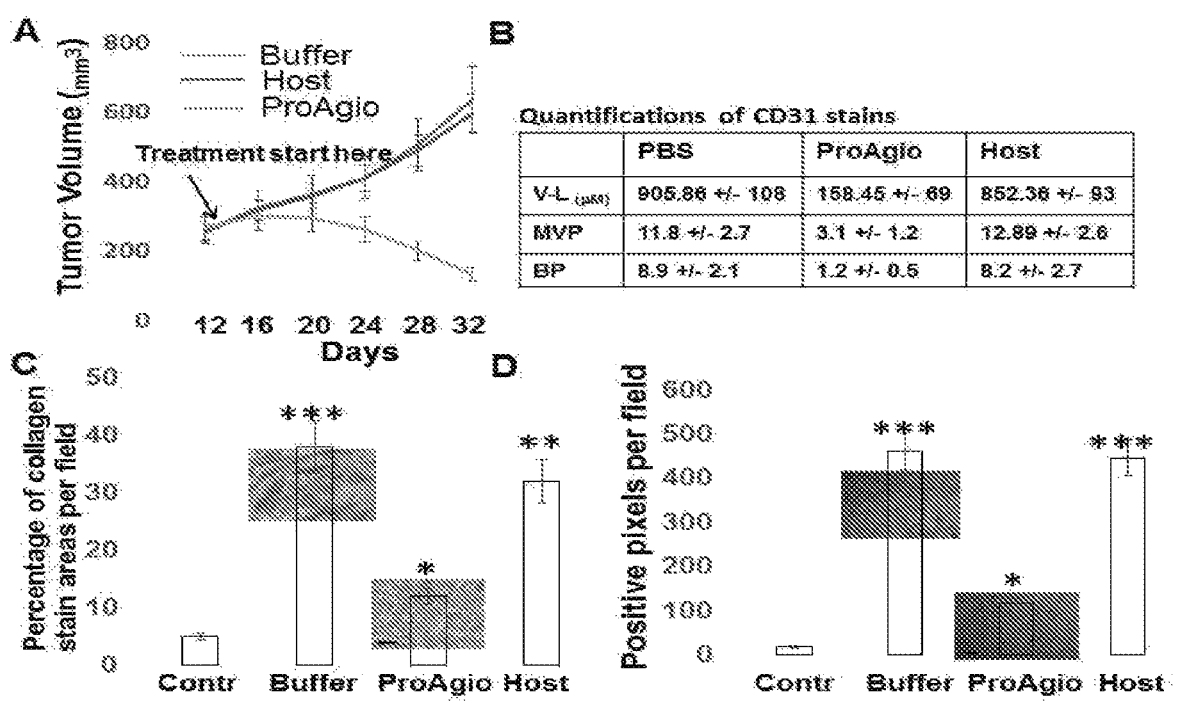
FIG. 56 shows that ProAgio reduces and prevents fibrosis in pancreatic cancer, which is formed by hard cell stroma and fiber forming cells.

FIG. 56 shows that ProAgio reduces and prevents fibrosis in pancreatic cancer, which is formed by cancer stroma and fiber forming cells. In pancreas cancer, activated fiber forming cells or pancreatic stellate cells, which have a high level of integrin alpha v beta 3. Section A shows growth of xenograft tumors of MIA-Paca-2 co-implanted with PaSC under the treatment of indicated agents was monitored by measuring tumor volumes every four days. PaSC were isolated from mouse pancreas and immortalized by a commercial hTERT kit. Treatments started when tumors reached average of 250 mm.sup.3 in size. Sections B, C, and D shows quantitative analyses of vessel lengths, densities, and branch points of the CD31 stains Section B, Sirius red stains Section C, and stains Section D of the tumor tissue sections. In section C, collagen contents are presented as % of collagen stained areas. In Section D, Positive α-SMA is presented as positive pixels per field. The control in (C) and (D) are the results from quantitation of sections of non-cancerous pancreas tissue. Error bars in (A), (C), and (D) are standard deviations from measurement of experimental of six mice. The p values were calculated using unpaired two-tailed Student t-test. In (C) and (D), * means $p<0.05$,  means $P<0.01$, and * means $P<0.001$. The images in (C) and (D) are representative of the indicated treatment groups.

Figures 57A, 57B:
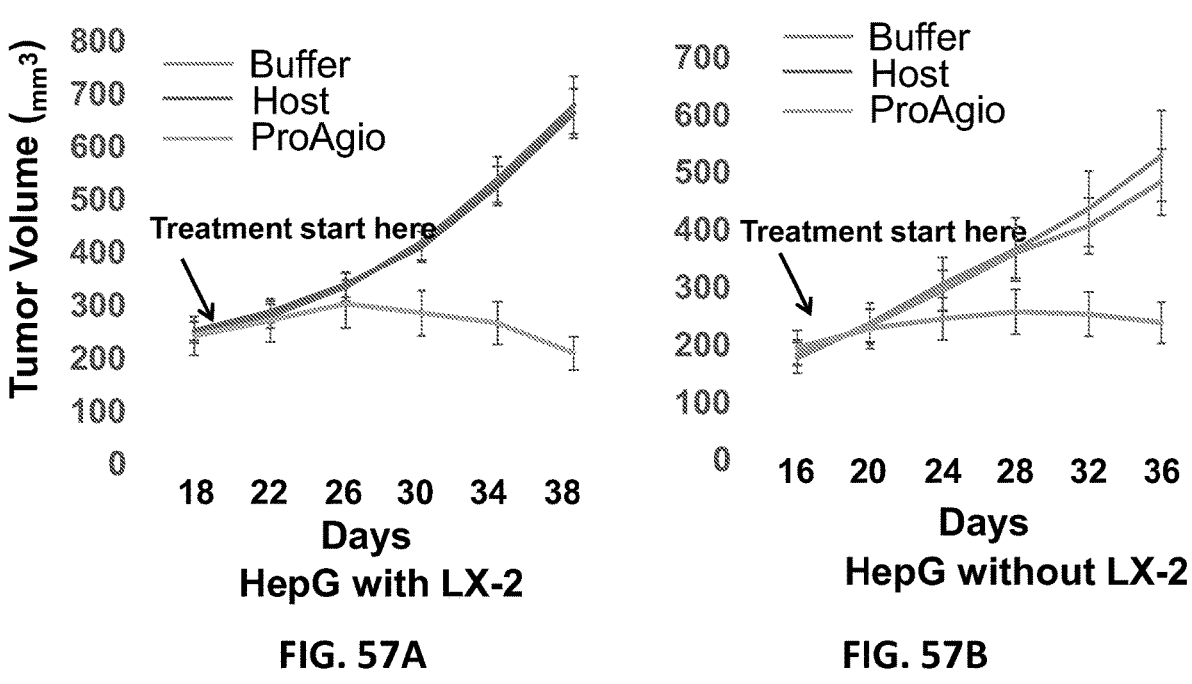
FIG. 57A though 57C show the results of ProAgio as treatment of liver cancer.
Figure 57C:
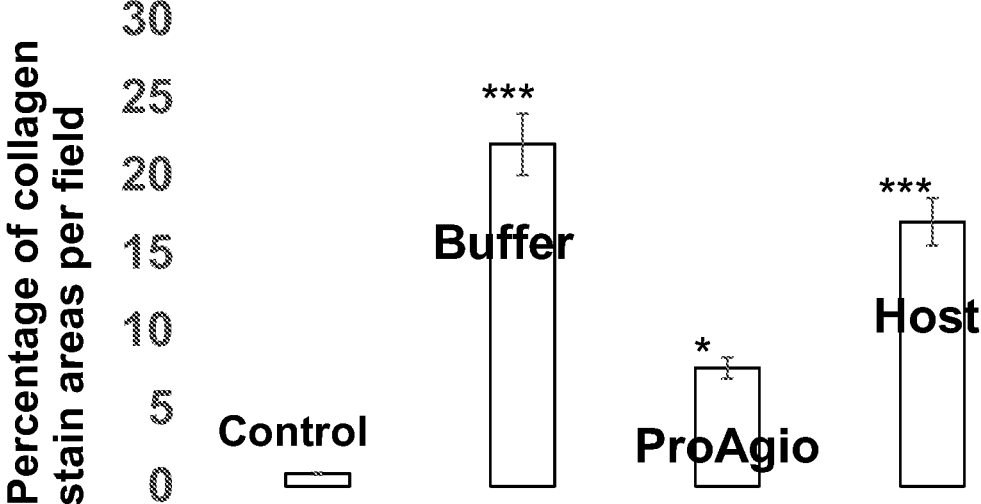

FIG. 57A, FIG. 57B, and FIG. 57C show that ProAgio reduces and prevents fibrosis in liver cancer. These figures show that ProAgio reduces and prevents fibrosis in liver cancer, and results in reduction in liver tumor volume. In liver cancer, activated fiber forming cells or hepatic stellate cells have a high level of expression of integrin alpha v beta 3. FIGS. 57A and 57B show the effect of ProAgio on liver cancer xenografts. These experiments were on xenografts of HepG tumor (six nude mice/group) and tumor started with $1×10^7$ HepG alone or half/half HepG+LX-2 cells. With treatments of 10 mg/kg one dose (i.p.) every two days for 20 days and at about 18 days after tumor inoculation, the tumor volume decreased with ProAgio. These cells (like myofibroblasts in other types of tumors) support and maintain the cancer cells in the tumor, such that their apoptosis causes tumors to shrink. Collagen contents are quantitated and presented as % of collagen stain areas. The quantitative measurement are manually counted in 319.8×319.8 mm2 view field using imaging-J. The quantization was average values of randomly selected 3 fields in position matched 4 sections from each tumor. Control are the results from sections of non-cancerous liver tissue. Error bars are standard deviations from measurement of experimental of six mice. FIG. 57C shows the collagen or fiber in tumors after treatment with ProAgio. A total 80 slides per animal group and three view fields per slide was examined and the control is Control is the stains of normal liver tissues. ProAgio treated liver cancer.

ProAgio may be applicable in treatment of other fibrosis diseases and treatment of osteoporosis. Further, ProAgio may be used in combination with other agents for treatment of Rheumatoid Arthritis.

An aspect of the present disclosure is the active site of the protein as disclosed herein, and its particularities as disclosed herein.

The specific examples disclosed herein are to be construed as merely illustrative, and not limitative of the remainder of the disclosure in any way whatsoever. Without further elaboration, it is believed that one skilled in the art can, based on the description herein, utilize the present disclosure to its fullest extent.

The disclosed examples are put forth so as to provide those of ordinary skill in the art with a complete disclosure and description of how to perform the methods and use the compositions and compounds disclosed and claimed herein. Efforts have been made to ensure accuracy with respect to numbers e.g., amounts, temperature, etc., but some errors and deviations should be accounted for. Unless indicated otherwise, parts are parts by weight, temperature is in degree C., and pressure is at or near atmospheric. Standard temperature and pressure are defined as 20 degree C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations, e.g., 1%, 2%, 3%, and 4%, and the sub-ranges, e.g., 0.5%, 1.1%, 2.2%, 3.3%, and 4.4%, within the indicated range. The term "about" can include .+−. 1%, .+−. 2%, .+−. 3%, .+−. 4%, .+−. 5%, .+−. 6%, .+−. 7%, .+−. 8%, .+−0.9%, or .+−. 10%, or more of the numerical value(s) being modified.

---

What is claimed is:

1. A method of decreasing excessive accumulation of fibrous material within the extracellular matrix in injured or damaged tissue of a subject comprising a. identifying the subject in need thereof, and b. administering to the subject a polypeptide that binds specifically to integrins $\alpha_v\beta_3$, comprising: a variant of domain 1 of cell adhesion protein (D1-CD2) having the amino acid of SEQ ID NO: 4, wherein the polypeptide specifically binds to integrin $\alpha_v\beta_3$ at $\beta$A domain in the region of $\alpha$2 helix, B—C loop and $\alpha$2-$\alpha$3 loop; and wherein the method decreases excessive accumulation of fibrous material in subjects having liver fibrosis, pancreatic fibrosis, or breast cancer associated fibrosis, and wherein the excess accumulation of fibrous material is not due to the subject having retrolental fibroplasia, idiopathic pulmonary fibrosis, neurofibroma or angiofibroma.

2. The method of claim 1, wherein the amino acid substitution on the polypeptide has hydrophilicity value ranges from about −2 to about +2 of the original amino acid of the wild-type D1-CD2.

3. The method of claim 1, wherein the variant comprises a sequence having substitution of L94N, E95D, K96V, I97C, F98N, D99F, L100A, K101S, and I102R.

4. The method of claim 1, wherein the variant has at least one intermolecular interaction with integrins $\alpha_v\beta_3$.

5. The method of claim 1, wherein the variant binds to integrins $\alpha v\beta 3$ at the $\beta$A groove.

6. The method of claim 1, wherein the variant is cross-linked to integrin av at TEMKQER (SEQ ID NO:1).

7. The method of claim 1, wherein the variant is PEGylated.

8. The method of claim 1, wherein the polyethylene glycol is PEG-20 kDa.

9. A method of inducing apoptosis in tissue of a subject, comprising administering a therapeutically effective amount of the pharmaceutical composition of a polypeptide that binds specifically to integrins $\alpha_v\beta_3$, comprising: a variant of domain 1 of cell adhesion protein (D1-CD2) having the amino acid of SEQ ID NO: 4, wherein the polypeptide specifically binds to integrin $\alpha_v\beta_3$ at $\beta$A domain in the region of $\alpha$2 helix, B—C loop and $\alpha$2-$\alpha$3 loop, and the polypeptide has a dissociation constant is less than 1 $\mu$M, and excess accumulation of fibrous material is not retrolental fibroplasia, idiopathic pulmonary fibrosis, neurofibroma or angiofibroma and the subject has liver fibrosis, pancreatic fibrosis or breast cancer associated fibrosis.

10. The method of claim 9, wherein the pharmaceutical composition is suitable for topical application, injection, oral administration, or time release dosage.

11. The method of claim 9, wherein the subject is a mammal.

12. The peptide as claimed in claim 9, wherein the $K_D$ is between about 1 $\mu$M and 1 pM.

* * * * *